(12) United States Patent
Carlson et al.

(10) Patent No.: US 7,416,791 B1
(45) Date of Patent: Aug. 26, 2008

(54) OSMIUM COMPLEXES AND RELATED ORGANIC LIGHT-EMITTING DEVICES

(75) Inventors: William B. Carlson, Seattle, WA (US); Gregory D. Phelan, Seattle, WA (US); Larry R. Dalton, Silverdale, WA (US); Kwan-Yue (Alex) Jen, Kenmore, WA (US); Xuezhong Jiang, Fogelsville, PA (US)

(73) Assignee: University of Washington, Seattle, WA (US)

( * ) Notice: Subject to any disclaimer, the term of this patent is extended or adjusted under 35 U.S.C. 154(b) by 595 days.

(21) Appl. No.: 10/460,054

(22) Filed: Jun. 11, 2003

Related U.S. Application Data

(60) Provisional application No. 60/388,124, filed on Jun. 11, 2002.

(51) Int. Cl.
*H01L 51/54* (2006.01)
*C09K 11/06* (2006.01)

(52) U.S. Cl. .................. 428/690; 428/917; 313/504; 313/506; 257/102; 257/103; 257/E51.044; 252/301.16; 252/301.35

(58) Field of Classification Search .............. None
See application file for complete search history.

(56) References Cited

U.S. PATENT DOCUMENTS

| | | | |
|---|---|---|---|
| 5,703,436 A | 12/1997 | Forrest et al. | |
| 5,707,745 A | 1/1998 | Forrest et al. | |
| 5,986,401 A | 11/1999 | Thompson et al. | |
| 6,013,982 A | 1/2000 | Thompson et al. | |
| 6,097,147 A | 8/2000 | Baldo et al. | |
| 6,166,489 A | 12/2000 | Thompson et al. | |
| 6,548,836 B1* | 4/2003 | Rubner et al. | 257/103 |
| 6,750,608 B2* | 6/2004 | Matsuura et al. | 313/504 |
| 6,835,473 B2* | 12/2004 | Matsuura et al. | 428/690 |
| 7,063,900 B2* | 6/2006 | Shiang et al. | 428/690 |
| 7,128,982 B2* | 10/2006 | Oshiyama et al. | 428/690 |
| 2003/0072964 A1 | 4/2003 | Kwong et al. | |
| 2003/0198831 A1 | 10/2003 | Oshiyama et al. | |

FOREIGN PATENT DOCUMENTS

WO    WO 01/41512 A1    6/2001

OTHER PUBLICATIONS

Creutz et al., "Lifetimes, Spectra and Quenching . . . Osmium (II)", Journal of the American Chemical Society, vol. 102, pp. 1309-1319 (1980).*
Ciana et al., "Synthesis and Characterization of a New Family of Luminescent . . . Os . . . Complexes . . . ", Inorg. Chem., vol. 29, pp. 2792-2798 (1990).*
Johnson et al., "Influence of Variations in the Chromophoric Ligand on the Properties of Metal-to-Ligand Charge-Transfer Excited States", Inorg. Chem., 27(18), pp. 3195-3200 (1988).*
Hector D. Abruna, "Electrochemiluminescence of Osmium Complexes", J. Electrochem. Soc.: Electrochemical Science and Technology, 132(4), pp. 842-849 (Apr. 1985).*
Bernhard, S., et al., "Efficient Electroluminescent Devices Based on a Chelated Osmium (II) Complex," *Adv. Mat.* 14(6):433-436, Mar. 18, 2002.
Carlson, B., et al., "Divalent Osmium Complexes: Synthesis, Characterization, Strong Red Phosphorescence, and Electrophosphorescence," *J. Am. Chem. Soc.* 124(47):14162-14172, 2002.
Jiang, X., et al., "Novel Europium and Osmium Complexes for Pure Red Light Emitting Diode Applications," *IUPAC 9th International Symposium on Macromolecule-Metal Complexes*, pp. 171-176.
Jiang, X., et al., "Red Electrophosphorescence From Osmium Complexes," *Appl. Phys. Lett.* 80(5):713-715, Feb. 4, 2002.
Jiang, X., et al., "Red-Emitting Electroluminescent Devices Based on Osmium-Complexes-Doped Blend of Poly(vinylnaphthalene) and 1,3,4-Oxadiazole Derivative," *Appl. Phys. Lett.* 81(17):3125-3127, Oct. 21, 2002.
Kim, J.H., et al., "Bright Red-Emitting Electrophosphorescent Device Using Osmium Complex as a Triplet Emitter," *Applied Physics Letters* 83(4):776-778, Jul. 28, 2003.
Kober, E.M., et al., "Highly Luminescent Polypyridyl Complexes of Osmium (II)," *J. Am. Chem. Soc.* 102(24):7383-7385, 1980.
Kober, E.M., et al., "Synthetic Routes to New Polypyridyl Complexes of Osmium (II)," *Inorganic Chem.* 27(25):4587-4598, Nov. 30, 1988.
Ma, Y., et al., "Electroluminescence from Triplet Metal-Ligand Charge-Transfer Excited State of Transition Metal Complexes," *Syn. Met.* 94:245-248, 1998.
Carlson, B., et al., "Novel Divalent Osmium Complexes: Synthesis, Characterization, Tuning of Emission, and Use in Organic Light Emitting Diodes," *Mat. Res. Soc. Smyp. Proc. 771*:363-368, 2003.
Carlson, B., et al., "Organic Electroluminescent Device Based Upon 4,7-bis(*p*-methoxyphenyl)-1,10-phenanthroline Containing Divalent Osmium Complexes," *Polymeric Materials Science and Engineering* 86:210-211, 2002.
Carlson, B., et al., "Organic Light Emitting Devices Based Upon Divalent Osmium Complexes. Part 1: Design, Synthesis, and Characterization of Osmium Complexes," in Zakya H. Kafafi and Homer Antoniadis (eds.), *Organic Light-Emitting Materials and Devices VI, Proceedings of SPIE*, The International Society for Optical Engineering, 2003, vol. 4800, pp. 93-104.
Jiang, X., et al., "Red Electrophosphorescence From Osmium Complexes," *Applied Physics Letters* 80(5):713-715, Feb. 4, 2002.

* cited by examiner

*Primary Examiner*—Marie R. Yamnitzky
(74) *Attorney, Agent, or Firm*—Christensen O'Connor Johnson Kindness PLLC

(57) ABSTRACT

Osmium complexes having the formula $[Os(II)(N\!-\!\!-\!N)_2L\!-\!\!-\!L]^{2+}\,2A^-$ (or $A^{2-}$), or $[Os(II)\,N\!-\!\!-\!N(L\!-\!\!-\!L)_2]^{2+}\,2A^-$ (or $A^{2-}$), where N—N is a bipyridine or phenanthroline ligand, L—L is a $\pi$-acid bidentate ligand, and A is counter ion.

24 Claims, 14 Drawing Sheets

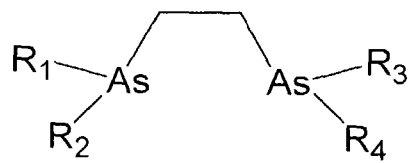
Figure 5A
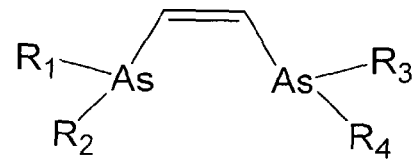
Figure 5B
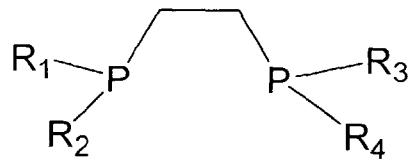
Figure 5C
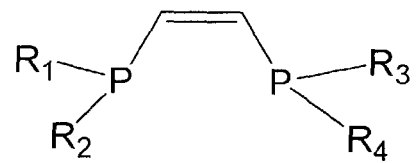
Figure 5D
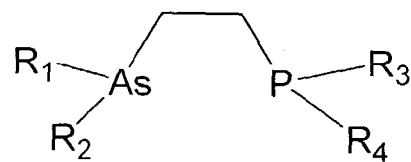
Figure 5E
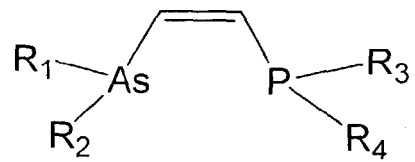
Figure 5F
FIGURES 5A-5F

23

24

25

| Complex | R | L-L |
|---|---|---|
| 1 | —⌬ | 23 |
| 2 | —⌬ | 24 |
| 3 | —⌬ | 25 |
| 4 | —⌬—O—⌬ | 25 |
| 5 | —⌬—⌬ | 23 |
| 6 | —⌬—⌬ | 25 |

| Complex | R | L-L |
|---|---|---|
| 7 | H | 24 |
| 8 | H | 25 |
| 9 | O-Me | 23 |
| 10 | O-Me | 24 |
| 11 | O-Me | 25 |
| 12 | Br | 25 |
| 13 | -⟨⟩-O-⟨⟩ | 25 |
| 14 | -⟨⟩⟨⟩ | 25 |

| | LC (nm) (ε) | ¹MLCT (nm) (ε) | ³MLCT (nm) (ε) | Emission[a] | τ ns[b] | Φ[c] |
|---|---|---|---|---|---|---|
| 1 | 262 (52,000), 306 (60,000) | 405 (16,000) | 520 (3700) | 650 | 410 | 0.19 |
| 2 | 301 (68,000) | 382 (17,000) | 484 (4500) | 623 | 520 | 0.23 |
| 3 | 304 (70,000) | 397 (18,000) | 512 (4700) | 640 | 460 | 0.25 |
| 4 | 301 (62,000), 330 (63,000) | 402 (22,000) | 518 (4300) | 645 | 470 | 0.27 |
| 5 | 308 (89,000), 331 (87,000) | 408 (26,000) | 508 (10,000) | 651 | 430 | 0.22 |
| 6 | 304 (91,000), 334 (88,000) | 402 (28,000) | 522 (11,000) | 643 | 450 | 0.28 |
| 7 | 282 (66,000) | 378 (21,000) | 507 (sh, 4,100) | 613 | 1810 | 0.33 |
| 8 | 279 (69,000) | 391 (22,000) | 524 (sh, 4,000) | 623 | 1530 | 0.38 |
| 9 | 274 (66,000), 331 (45,000) | 397 (36,000) | 505 (sh, 9,000) | 635 | 1200 | 0.27 |
| 10 | 269 (69,000), 327 (52,000) | 364 (50,000) | 487 (sh, 9,000) | 611 | 1970 | 0.36 |
| 11 | 273 (71,000), 329 (43,000) | 391 (39,000) | 500 (sh, 8,000) | 629 | 1550 | 0.45 |
| 12 | 290 (75,000) | 391 (28,000) | 500 (sh, 6,300) | 635 | 1400 | 0.39 |
| 13 | 273 (101,000); 344 (49,000) | 393 (44,000) | 500 (sh, 7,500) | 637 | 1310 | 0.40 |
| 14 | 283 (108,000); 331 (51,000) | 374 (52,000) | 500 (sh, 8,400) | 637 | 1260 | 0.41 |

[a]Emission peak. [b]Luminescence lifetime. [c]Luminescence quantum yield.

FIGURE 11

| Os complex | X⁻ | Device | $V_l$ (V) [a] | $B_{max}$ (cd/m$^2$) [b] | $\eta_{max}$ [c] |
|---|---|---|---|---|---|
| 1 | HFB | I | 9.3 | 310 | 0.64% |
| 2 | HFB | I | 7.5 | 260 | 0.27% |
| 2 | Ts | I | 8.7 | 970 | 0.27% |
| 3 | HFB | I | 7.6 | 410 | 0.60% |
| 3 | Ts | I | 7.5 | 725 | 0.42% |
| 4 | Tf | I | 8.4 | 600 | 0.32% |
| 6 | Tf | I | 6.7 | 799 | 0.28% |
| 7 | Tf | I | 6.9 | 750 | 0.20% |
| 8 | Tf | I | 6.4 | 1030 | 0.31% |
| 9 | Ts | I | 9.4 | 460 | 0.39% |
| 10 | Ts | I | 7.6 | 1430 | 0.48% |
| 11 | Ts | I | 8.0 | 1210 | 0.78% |
| 12 | Ts | I | 7.5 | 760 | 0.29% |
| 12 | PF$_6$ | I | 6.0 | 710 | 0.19% |
| 12 | PF$_6$ | II | 12.2 | 470 | 0.79% |
| 13 | Ts | I | 8.2 | 780 | 0.31% |
| 14 | Ts | I | 7.8 | 960 | 0.45% |
| 14 | PF$_6$ | I | 7.0 | 1090 | 0.48% |
| 14 | PF$_6$ | II | 14.2 | 870 | 2.2% |

[a] Voltage needed for brightness of 1 cd/m$^2$. [b] Maximum brightness. [c] Maximum external quantum efficiency.

FIGURE 12

OSMIUM COMPLEXES AND RELATED ORGANIC LIGHT-EMITTING DEVICES

CROSS-REFERENCE TO RELATED APPLICATION

The present application claims the benefit of U.S. Patent Application No. 60/388,124, filed Jun. 11, 2002.

FIELD OF THE INVENTION

The present invention relates to electroluminescent osmium complexes and organic light-emitting diode devices that include the osmium complexes.

BACKGROUND OF THE INVENTION

Rapid growth in the use of organic light-emitting devices (OLEDs) is expected in the coming years due to their potential application in large screen flat panel displays. For full-color displays, efficient light-emitting diodes (LEDs) emitting three primary colors (i.e., blue, green and red) are required. However, obtaining strong red emission from conjugated polymers or small molecules is generally difficult because of the difficulty in obtaining sufficient conjugation length, and the gap law.

The use of triplet-based emitting centers in organic and polymer LEDs eliminates the 25 percent limit for maximum internal quantum efficiency, which is the expected singlet exciton fraction generated by electrical injection, and potentially allows for displays with 100 percent internal quantum efficiency. Strong back bonding with a metal center that exhibits a large spin orbit coupling constant facilitates intersystem crossing by breaking down the spin selection rules, leading to strong triplet state emission. This provides a possibility to design high efficiency OLED devices by using phosphorescent materials. Triplet-harvesting red and green LEDs based on platinum and iridium complexes have demonstrated very high external quantum efficiency. Europium complexes also show triplet emission and have also been used in red OLEDs. The characteristic of the lowest excited states (triplet states) of these heavy-metal complexes can be systematically varied from largely ligand-centered (LC) to metal-to-ligand-charge-transfer (MLCT) character. The triplet emission character depends upon the strength of the back bonding between the metal center and the ligand, and the relative energies of the $\pi^*$ (LC) transition versus the $d\pi^*$ (MLCT) transition. The emission of europium complexes (sharp bands at around 615 nm) is completely inner shell electronic f to d transitions and is determined by the energetics of the central $Eu^{3+}$ ion. The emission from platinum (II) porphyrins is ligand based, and iridium (III) complexes are largely ligand-based, although MLCT complexes have been reported for some iridium complexes as well. Luminescence of certain osmium (II) complexes being reported is from the MLCT state. Furthermore, these third row heavy-metal complexes tend to be thermally, chemically, and photochemically robust, which is favorable for device stability. Extremely long device lifetime has been reported for a triplet LED device using platinum octaethylporphorin (PtOEP) as LC emitting center with a 298° K triplet lifetime of about 50 µs. The long device lifetime is speculated to be an intrinsic property of electrophosphorescent LEDs, where radiative phosphors significantly shorten the lifetime of potentially reactive triplet states in the conductive host material. Due to strong back bonding from osmium to the ligands, the osmium complex triplet MLCT emission has a very short lifetime (from about 0.6 to about 1.8 µs).

Recently, red electrophosphorescence from osmium complexes has been reported. Jen et al., Applied Physics Letters, Vol. 80, No. 5, Feb. 4, 2002. Red electrophosphorescence from light-emitting diodes based on osmium complexes was achieved using in situ polymerized tetraphenyldiaminobiphenyl-containing polymers as the hole-transporting layer and osmium complexes doped blend of poly(N-vinylcarbazole) and 2-t-butylphenyl-1,3,4-oxadiazole as the emitting layer. The emission ranged from 620 to 650 mm. Because the emission originates from triplet metal-to-ligand-charge-transfer excited state, the emission, ranging from 620 to 650 nm, was tuned by changing the structures of the ligands. The peak external quantum efficiency and brightness achieved from the complexes were 0.82% and 970 $cd/m^2$, respectively. The Commission Internationale de l'Eclairage (CIE) chromaticity coordinates (x, y) for the best red emission from the complexes are (0.65, 0.33).

The reported osmium complexes were bis(4,4'-diphenyl-2,2'-bipyridyl) osmium (II) complexes. The complexes included either a phosphine or arsine bidentate ligand: 1,2-bis(diphenylarseno)ethane; cis-1,2-bis(diphenylarseno)ethylene; or cis-1,2-bis(diphenylphosphino)ethylene. The complexes further included two negatively charged counter ions: heptafluorobutylate ($CF_3CF_2CF_2CO_2-$) or p-toluene-sulfonate ($CH_3C_6H_4SO_3-$).

Despite the advances in the development in osmium complexes for use in OLEDs, there exists a need for osmium complexes having greater brightness and higher quantum yields compared to existing osmium complexes. The present invention seeks to fulfill this need and provides further related advantages.

SUMMARY OF THE INVENTION

In one aspect of the present invention, osmium complexes are provided. In one embodiment, the osmium complexes have the formula $[Os(II) (N-N)_2L-L]^{2+}$ $2A^-$ (or $A^{2-}$) where N—N is a bipyridine or phenanthroline ligand, L—L is a π-acid bidentate ligand, and A is a counter ion. Complexes having the formula $[Os(II) (N-N)_2L-L]^{2+}$ $2A^-$ (or $A^{2-}$) have red emission. In another embodiment, the osmium complexes have the formula $[Os(II) N-N(L-L)_2]^{2+}+2A^-$ (or $A^{2-}$), where N—N is a bipyridine or phenanthroline ligand, L—L is a π-acid bidentate ligand, and A is counter ion. Complexes having the formula $[Os(II) N-N(L-L)_2]^{2+}$ $2A^-$ (or $A^{2-}$) have green emission.

In another aspect, the present invention provides light-emitting devices that include the osmium complexes. In one embodiment, the device is a single-layer device. In other embodiments, the device includes more than one layer, for example, a double-layer device or a triple-layer device.

In other aspects of the invention, methods for making the osmium complexes and methods for making the devices that include the osmium complexes are also provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 5A-5G illustrate the chemical structures of π-acid ligands of the osmium complexes of the invention;

FIG. 11 is a table summarizing the optical properties for representative osmium complexes of the invention: absorption maxima for various ligand and charge transfer bands (nm); extinction coefficient ($\epsilon$); emission wavelength maxima (nm); luminescence lifetime ($\tau$, ns); and luminescence quantum yield ($\Phi$);

FIG. 12 is a table comparing the performance properties for LEDs doped with representative osmium complexes of the invention and including either PVK:PBD or PVN:PBD: ITO/BTPD-PFCB/Os complex/PVK:PBD/Ca (Type I); or ITO/BTPD-PFCB/Os complex/PVN:PBD/Ca (Type II): voltage needed for 1 cd/m² brightness ($V_1$, V); maximum brightness ($B_{max}$, cd/m²); and maximum external quantum efficiency ($\eta_{max}$); FIG. 13A is an electroluminescent cell (a single layer device); FIG. 13B is a double layer device; and FIG. 13C is a triple layer device.

DETAILED DESCRIPTION OF THE PREFERRED EMBODIMENT

In one aspect of the present invention, osmium complexes are provided. In one embodiment, the osmium complexes have the formula [Os (II) (N—N)$_2$L—L]$^{2+}$ 2A$^-$ (or A$^{2-}$) where N—N is a bipyridine or phenanthroline ligand, L—L, is a strong π-acid ligand, and A is either a singly or doubly negatively charged counter ion. Complexes having the formula [Os(II) (N—N)$_2$L—L]$^{2+}$ 2A$^-$ (or A$^{2-}$) have red emission. In another embodiment, the osmium complexes have the formula [Os(II) N—N(L—L)$_2$]$^{2+}$ 2A$^-$ (or A$^{2-}$), where N—N is a bipyridine or phenanthroline ligand, L—L, is a strong π-acid ligand, and A is either a singly or doubly negatively charged counter ion. Complexes having the formula [Os(II) N—N(L—L)$^2$]$^{2+}$ 2A$^-$ (or A$^{2-}$) have green emission.

Figure 1:
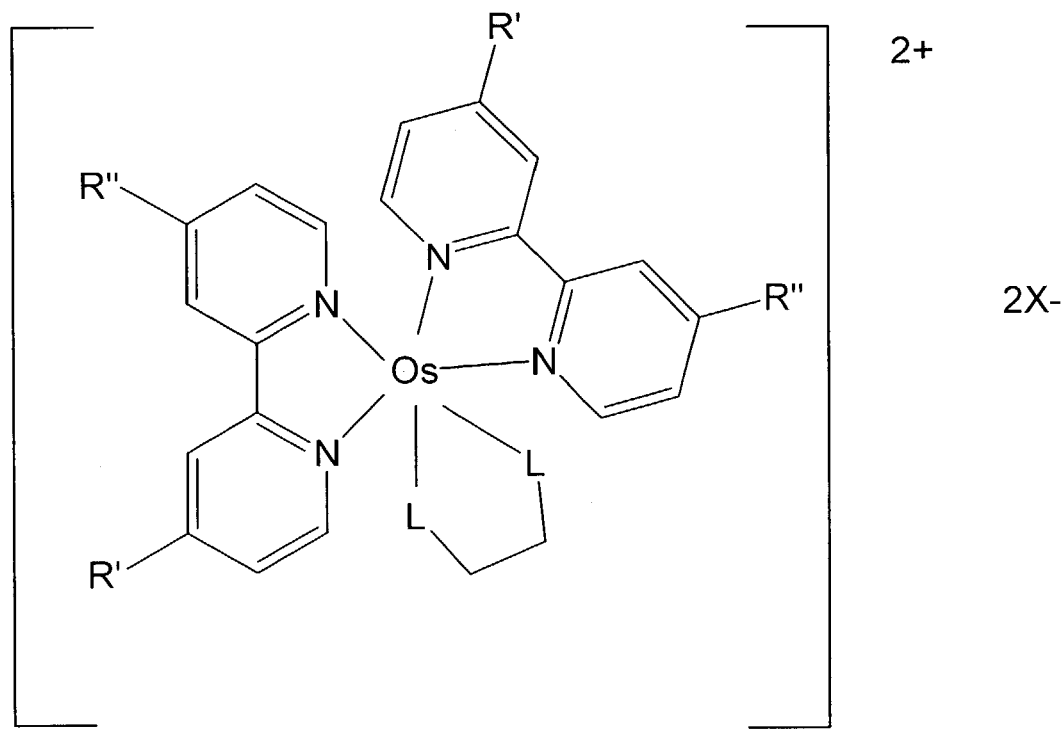
FIG. 1 is the chemical structure of a representative red-emitting osmium complex of the invention having bipyridine ligands.

The chemical structure of a representative red-emitting osmium complex of the invention having bipyridine ligands is shown in FIG. 1.

Figure 2:
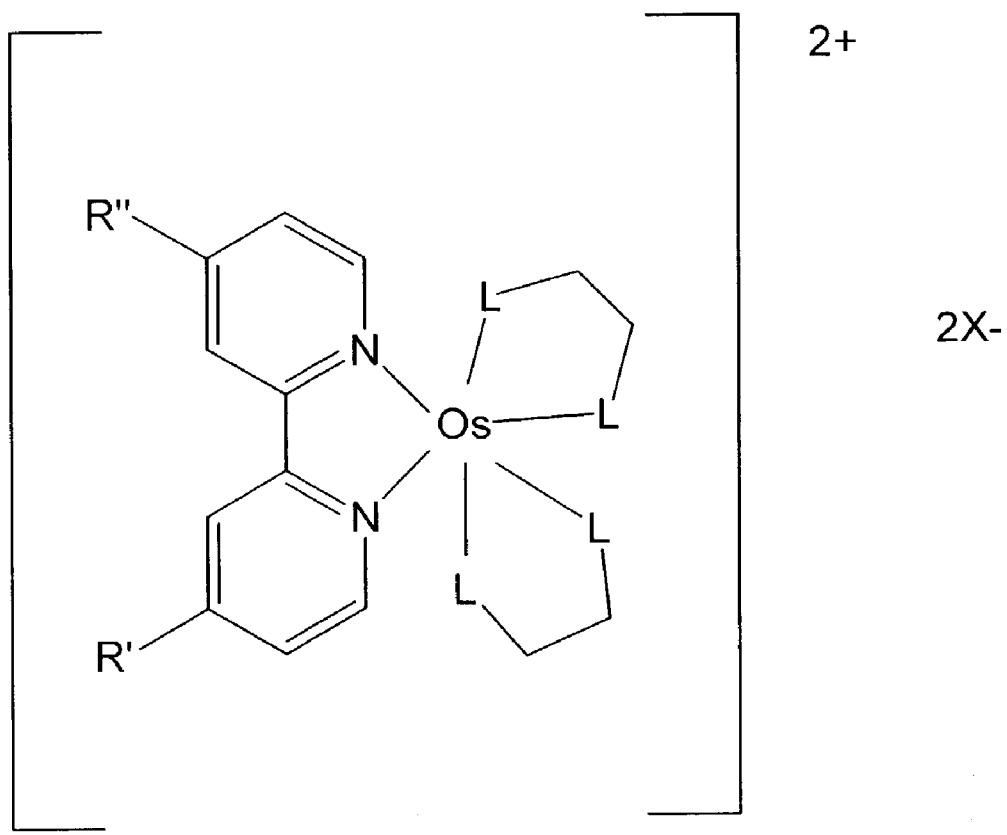
FIG. 2 is the chemical structure of a representative green-emitting osmium complex of the invention having bipyridine ligands.

The chemical structure of a representative green-emitting osmium complex of the invention having a bipyridine ligand is shown in FIG. 2.

Figure 3:
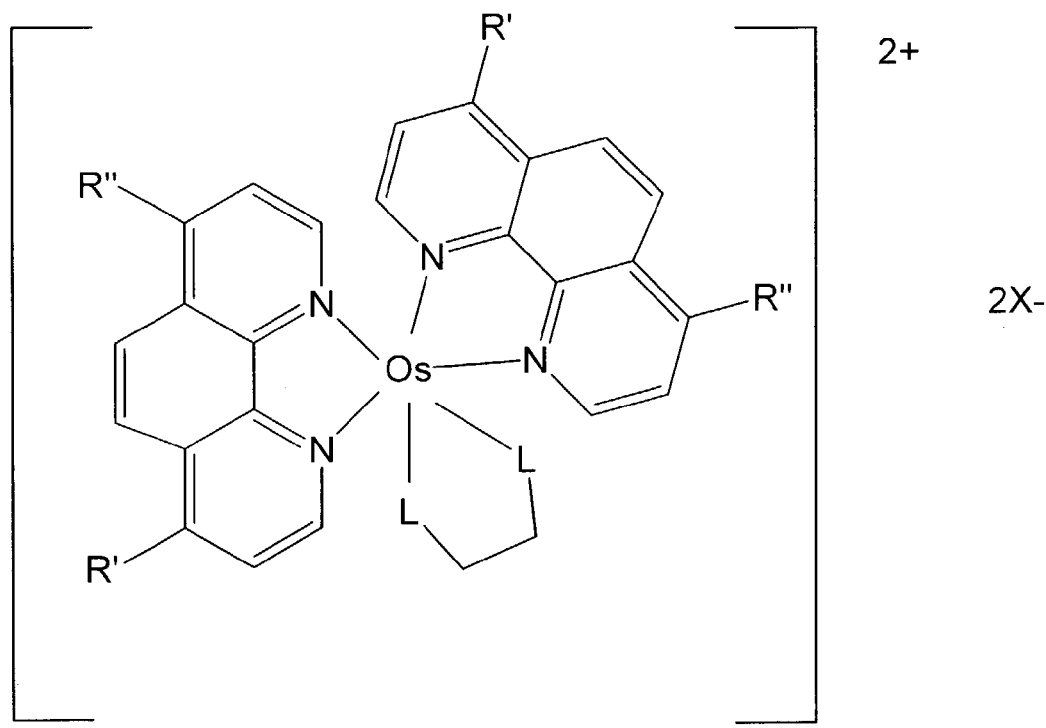
FIG. 3 is the chemical structure of a representative red-emitting osmium complex of the invention having phenanthroline ligands.

The chemical structure of a representative red-emitting osmium complex of the invention having phenanthroline ligands is shown in FIG. 3.

Figure 4:
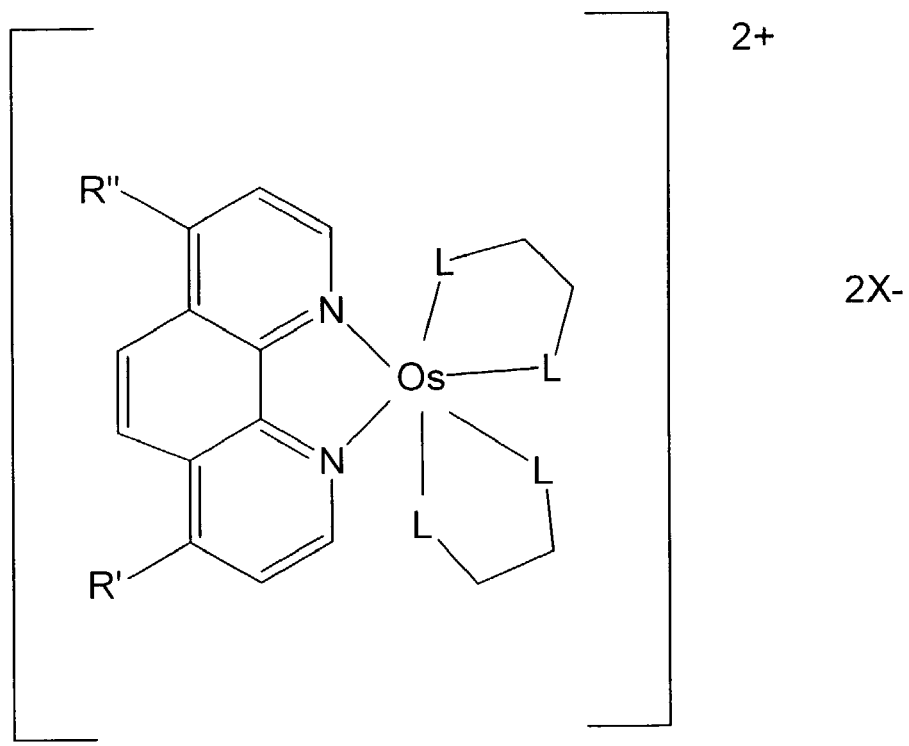
FIG. 4 is the chemical structure of a representative green-emitting osmium complex of the invention having phenanthroline ligands.

The chemical structure of a representative green-emitting osmium complex of the invention having a phenanthroline ligand is shown in FIG. 4.

In FIGS. 1-4, bipyridine and phenanthroline substituents are designated R' and R", the π-acid ligand is L—L moiety, and the counter ion is X$^-$.

As noted above, the osmium complexes of the invention include a divalent osmium metal center coordinated with either one or two bipyridine or phenanthroline ligands, one or two π-acid ligands, and include either two singly negatively charged counter ions, or one doubly charged counter ion.

In one embodiment, the osmium complex includes two bipyridine ligands. In this embodiment, at least one of the bipyridine ligands is substituted. In another embodiment, the osmium complex includes two phenanthroline ligands. In this embodiment, the phenanthroline ligand may be substituted or unsubstituted. In another embodiment, the osmium complex includes one bipyridine ligand and one phenanthroline ligand. In this embodiment, the bipyridine and phenanthroline ligands may be substituted or unsubstituted. When the osmium complex includes two bipyridine ligands, or two phenanthroline ligands, or one bipyridine and one phenanthroline ligand, the complex has a red emission. These complexes also include one π-acid bidentate ligand, and one or two counter ions. FIGS. 1 and 3 illustrate representative osmium complexes of the invention that have red emission.

In one embodiment, the osmium complex includes one bipyridine ligand. In this embodiment, the bipyridine ligand may be substituted or unsubstituted. In another embodiment, the osmium complex includes one phenanthroline ligand. In this embodiment, the phenanthroline ligand may be substituted or unsubstituted. When the osmium complex includes one bipyridine ligand, or one phenanthroline ligand, the complex has a green emission. These complexes also include two π-acid bidentate ligands, and one or two counter ions. FIGS. 2 and 4 illustrate representative osmium complexes of the invention that have red emission.

In certain embodiments, the osmium complex includes a bipyridine ligand. Suitable bipyridine ligands include substituted and unsubstituted bipyridine ligands. In one embodiment, the bipyridine is a 2,2'-bipyridine. The bipyridine ligand can be substituted at one or more positions with one or more substituents. For a bipyridine ligand substituted with more than one substituent, the substituents may the same or different. The bipyridine ligand can be substituted at any position so long as the substitution does not limit the ligands ability to form a stable complex with the osmium metal center. In one embodiment, the bipyridine is disubstituted. In one embodiment, the bipyridine is symmetrically disubstituted (e.g., 4,4'-disubstituted-2,2'-bipyridine).

Suitable bipyridine substituents include substituted or unsubstituted alkyl, aryl, arylalkyl, alkenyl, alkoxy, amino, alkylamino, dialkylamino, and halogen. In one embodiment, the bipyridine substituent is an aryl group, such as a phenyl, biphenyl, biphenyl ether, polyphenyl, quinolinyl, napthyl, and groups derived from polynuclear aromatic compounds such as pyrene and anthracene. The aryl groups may be further substituted.

In certain embodiments, the osmium complex includes a phenanthroline ligand. Suitable phenanthroline ligands include substituted and unsubstituted phenanthroline ligands. In one embodiment, the phenanthroline is a 1,10-phenanthroline. The substituted phenanthroline ligand can be substituted at one or more positions with one or more substituents. For a phenanthroline ligand substituted with more than one substituent, the substituents may the same or different. The phenanthroline ligand can be substituted at any position so long as the substitution does not limit the ligands ability to form a stable complex with the osmium metal center. In one embodiment, the phenanthroline is disubstituted. In one embodiment, the phenanthroline is symmetrically disubstituted (e.g., 4,7-disubstituted-1,10-phenanthroline).

Suitable phenanthroline substituents include substituted or unsubstituted alkyl, aryl, arylalkyl, alkenyl, alkoxy, amino, alkylamino, dialkylamino, and halogen. In one embodiment, the bipyridine substituent is an aryl group, such as a phenyl, biphenyl, biphenyl ether, polyphenyl, quinolinyl, napthyl, and groups derived from polynuclear aromatic compounds such as pyrene and anthracene. The aryl groups may be further substituted. In one embodiment, the phenanthroline substituent is an aryl group, such as a biphenyl ether or naphthyl. The aryl groups may be further substituted. In another embodiment, the phenanthroline substituent is an alkoxy group, such as methoxy. In another embodiment, the phenanthroline substituent is a halogen, such as bromo.

Figure 5G:
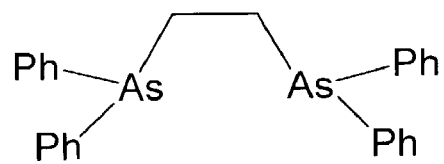
Figure 5G:
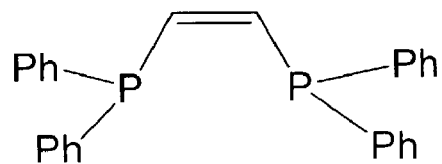
Figure 5G:
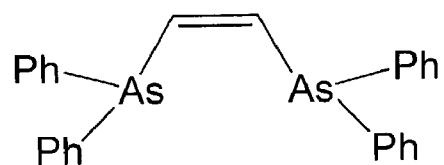

The osmium complexes of the invention include a π-acid bidentate ligand. The bidentate ligand includes two atoms that coordinate with osmium. In one embodiment, the atom that coordinates with osmium is a phosphorous atom, and in another embodiment, the atom that coordinates with osmium is an arsenic atom. Other suitable atoms that coordinate with osmium that can be included in the π-acid bidentate ligand useful in the complexes of the invention include antimony, sulfur, selenium, bismuth, and tin. In one embodiment, the bidentate ligand includes two phosphorous atoms. In one embodiment, the bidentate ligand includes two arsenic atoms. In another embodiment, the bidentate ligand includes one phosphorous atom and one arsenic atom. In one embodiment of the bidentate ligand, the atoms that coordinate osmium are separated by two carbon atoms. In one embodiment, the atoms that coordinate osmium are separated by an ethane group (e.g., —CH$_2$CH$_2$—). In another embodiment, the atoms that coordinate osmium are separated by an ethene group (e.g., —CH=CH—). In other embodiments, the atoms that separate the atoms that coordinate osmium are part of an aromatic group such as benzene or thiophene. In these embodiments, the ethane, ethene, and aromatic groups may be further substituted. The atoms that coordinate osmium can also be substituted. Suitable substituents include aryl groups, such as phenyl groups. Representative bidentate ligands include 1,2-bis(diphenylarseno)ethane; 1,2-bis(diphenylphosphino)ethane; cis-1,2-bis(diphenylphosphino)ethylene; cis-1,2-bis(diphenylarsine)ethylene; 1-diphenylarseno-2-diphenyl-phosphino(ethane); and cis-(1-diphenylarseno)-(2-diphenyl-phosphino)ethylene. FIGS. 5A-5F illustrate the chemical structures of 1-acid ligands of the osmium complexes of the invention. In FIGS. 5A-5F, R$_1$-R$_4$ may be the same or different. Suitable R$_1$-R$_4$ groups include alkyl and aryl groups. FIG. 5G illustrates the chemical structures of three representative π-acid bidentate ligand (Compounds 23-25). In FIG. 5G, Ph represents a phenyl group.

The osmium complexes of the invention include divalent osmium, Os (II), and also include one or more counter ions. In one embodiment, the osmium complex includes two singly negatively charged counter ions (2A$^-$), In another embodiment, the osmium complex includes one doubly negatively charged counter ion (A$^{2-}$). Representative counter ions include heptafluorobutyrate (HFB, CF$_3$CF$_2$CF$_2$CO$_2^-$), triflate (Tf, CF$_3$SO$_3^-$), tosylate (Ts, CH$_3$C$_6$H$_4$SO$_3^-$), and hexafluorophosphate (PF$_6^-$).

The following definitions are provided to better understand the invention.

The term "alkyl", alone or as part of another group, refers to a monovalent alkane (hydrocarbon) derived radical containing from 1 to 12 carbon atoms unless otherwise defined. An alkyl group is an optionally substituted straight, branched, or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include, but are not limited to, one or more of the following groups: halo (such as F, Cl, Br, I), haloalkyl (such as —CCl$_3$ or —CF$_3$), alkoxy, alkylthio, hydroxy, carboxy (—COOH), alkyloxycarbonyl (—C(O)R), alkylcarbonyloxy (—OCOR), amino (—NH2), carbamoyl (—NHCOOR— or —OCONHR—), urea (—NHCONHR—), or thiol (—SH). Alkyl groups as defined may also comprise one or more carbon to carbon double bonds or one or more carbon to carbon triple bonds. The alkyl group may also be a cycloalkyl group.

The term "alkenyl", alone or as part of another group, refers to a hydrocarbon radical straight, branched or cyclic containing from 2 to 12 carbon atoms and at least one carbon to carbon double bond.

The numbers in the subscript after the symbol "C" define the number of carbon atoms a particular group can contain. For example "C1-6 alkyl" means a straight or branched saturated carbon chain having from one to six carbon atoms; examples include methyl, ethyl, n-propyl, isopropyl, n-butyl, sec-butyl, isobutyl, tbutyl, n-pentyl, sec-pentyl, isopentyl, and n-hexyl. Depending on the context, "C1-6 alkyl" can also refer to C1-6 alkylene which bridges two groups; examples include propane-1,3-diyl, butane-1,4-diyl, 2-methyl-butane-1,4-diyl. "C2-6 alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "C2-6 alkenyl" can also refer to C2-6 alkenediyl which bridges two groups; examples include ethylene-1,2-diyl (vinylene), 2-methyl butene-1,4-diyl, 2-hexene-1,6-diyl.

The term "cycloalkyl", alone or as part of another group, is a specie of alkyl containing from 3 to 15 carbon atoms, without alternating double bonds between carbon atoms. The group may contain from 1 to 4 rings. Exemplary unsubstituted such groups include cyclopropyl, cyclobutyl, cyclopentyl, cyclohexyl, and adamantyl. Exemplary substituents include one or more of the following groups: halogen, alkyl, alkoxy, alkyl hydroxy, amino, nitro, cyano, thiol and/or alkylthio.

The terms "alkoxy" or "alkylthio", alone or as part of another group, denote an alkyl group as described above bonded through an oxygen linkage (—O—) or a sulfur linkage (—S—), respectively.

The term "arylalkyl", alone or as part of another group, denotes an aromatic ring bonded to an alkyl group as described above.

The term "aryl", alone or as part of another group, refers to monocyclic or bicyclic aromatic rings, e.g., phenyl, substituted phenyl, and the like, as well as groups which are fused, e.g., napthyl, phenanthrenyl, and the like. An aryl group thus contains at least one ring having at least 6 atoms, with up to five such rings being present, containing up to 22 atoms therein, with alternating double bonds between adjacent carbon atoms or suitable heteroatoms. Aryl groups may optionally be substituted with one or more groups including, but not limited to, halogen, alkyl, alkoxy, hydroxy, carboxy, carbamoyl, alkyloxycarbonyl, nitro, trifluoromethyl, amino, cycloalkyl, cyano, alkyl S(O)$_m$ (m=0, 1, 2), or thiol.

The term "cycloalkyl", alone or as part of another group, refers to fully saturated and partially unsaturated hydrocarbon rings of 3 to 9, preferably 3 to 7 carbon atoms. A cycloalkyl may be substituted. A substituted cycloalkyl refers to such rings having one, two, or three substituents, preferably one selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, C(=O)alkyl, keto, =N—OH, —N alkyl, aryl, heteroaryl, heterocyclo, a five or six membered ketal (e.g., 1,3-dioxolane or 1,3-dioxane), —NR'R", —C(=O)NR'R", —$CO_2$NR'R", —NR'$CO_2$R", —NR'C(=O)R", —$SO_2$NR'R", and NR'$SO_2$R", wherein each of R' and R" is independently selected from hydrogen, alkyl, substituted alkyl, and cycloalkyl, or R' and R" together form a heterocyclo or heteroaryl ring.

The term "heteroaryl", alone or as part of another group, refers to substituted and unsubstituted aromatic 5 or 6 membered monocyclic groups, 9 or 10 membered bicyclic groups, and 11 to 14 membered tricyclic groups which have at 6 least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups that are bicyclic or tricyclic must include at least one fully aromatic ring, but the other fused ring or rings may be aromatic or nonaromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, hydroxy, alkoxy, thioalkyl, —$CO_2H$, —C(=O)H, —$CO_2$alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like. Exemplary tricyclic heteroaryl groups include carbazolyl, benzidolyl, phenanthrollinyl, acridinyl, phenanthridinyl, xanthenyl and the like.

The term "halogen" or "halo" refers to chlorine, bromine, fluorine or iodine selected on an independent basis.

The term "amino", alone or as part of another group, refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl, or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

Figure 6:
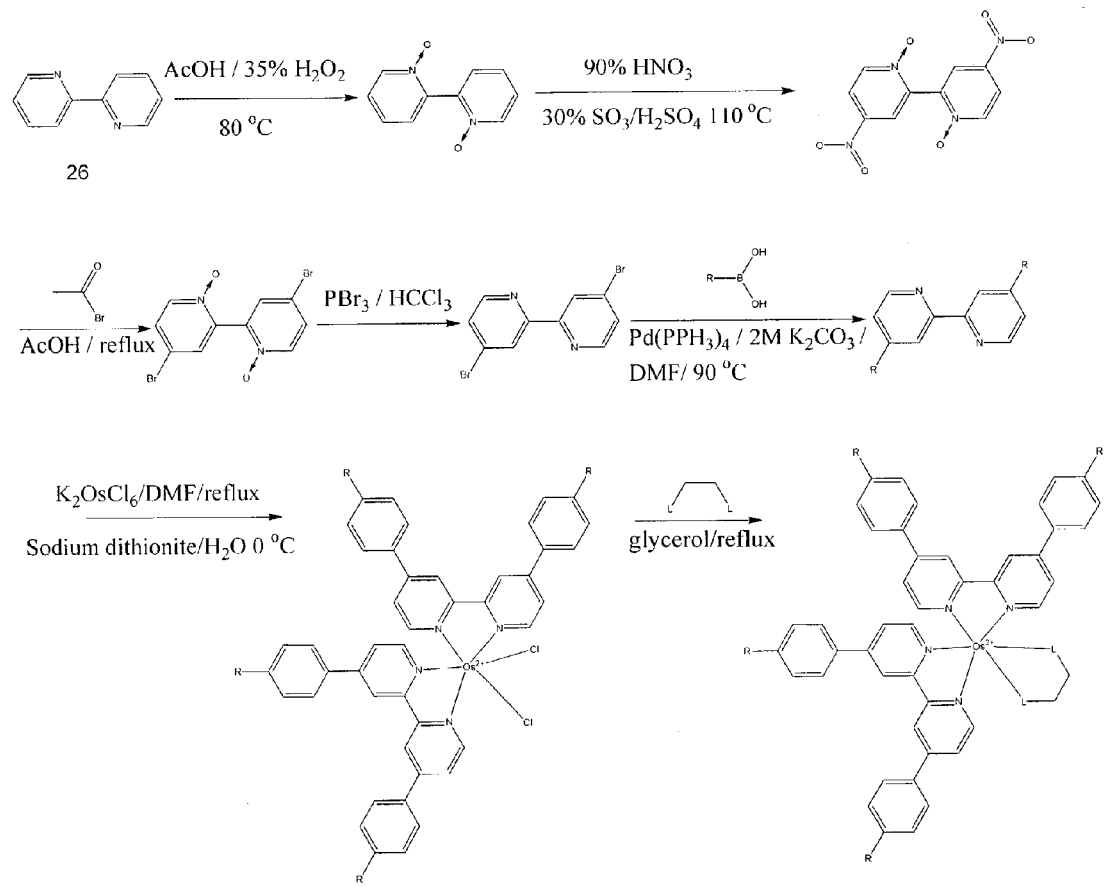
FIG. 6 is a synthetic scheme for the preparation of representative osmium complexes having bipyridine ligands.
Figure 7:
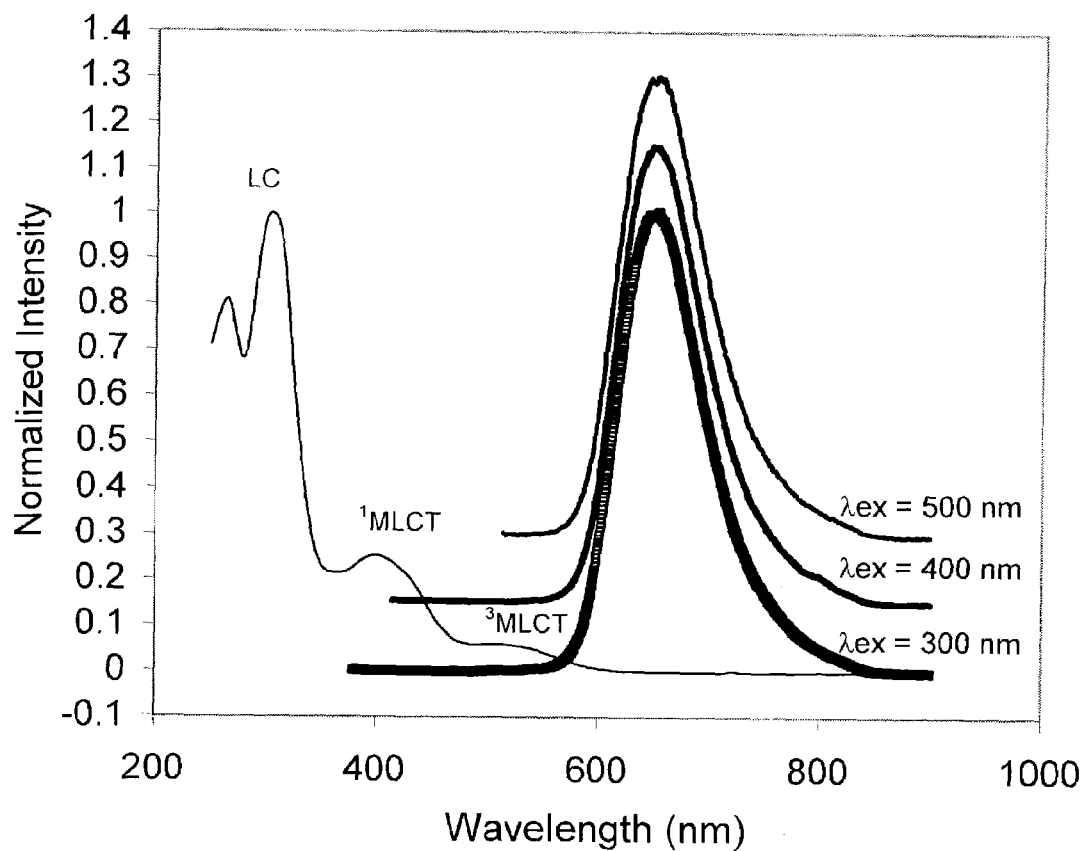
FIG. 7 is an absorption spectrum of a representative osmium complex of the invention with emission spectra as a function of excitation wavelength.

Red-Emitting Osmium Complexes. The preparation of representative osmium complexes having bipyridine ligands is shown in FIG. 6. An absorption spectrum of a representative osmium complex of the invention with emission spectra as a function of excitation wavelength is shown in FIG. 7.

Figure 8:
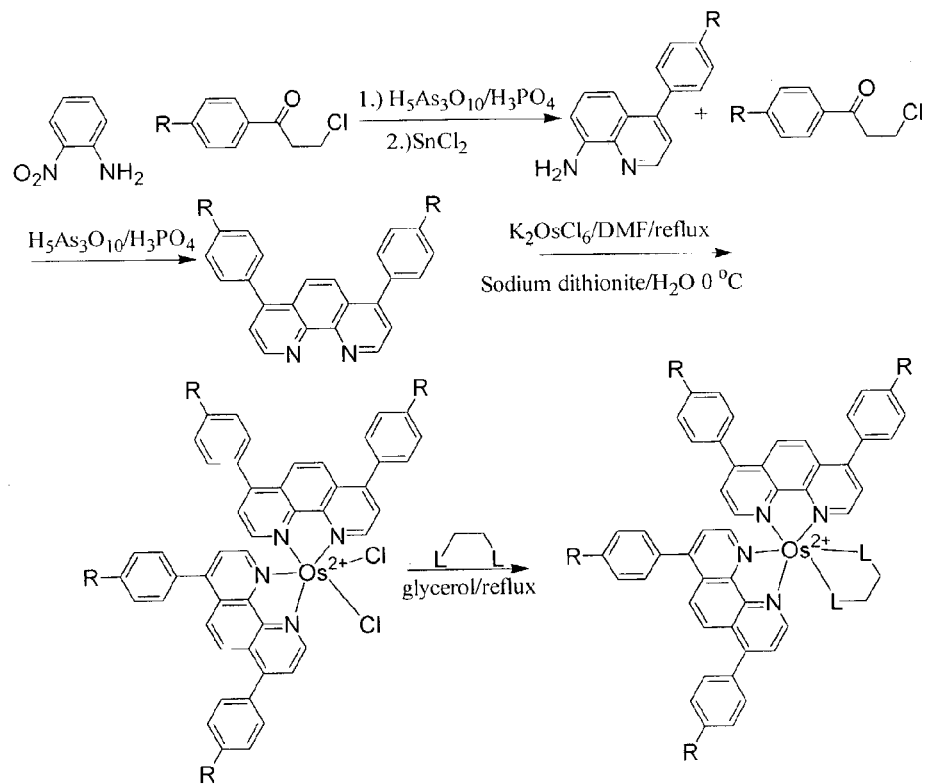
FIG. 8 is a synthetic scheme for the preparation of representative osmium complexes having phenanthroline ligands.

The preparation of representative osmium complexes having phenanthroline ligands is shown in FIG. 8.

Figure 9:
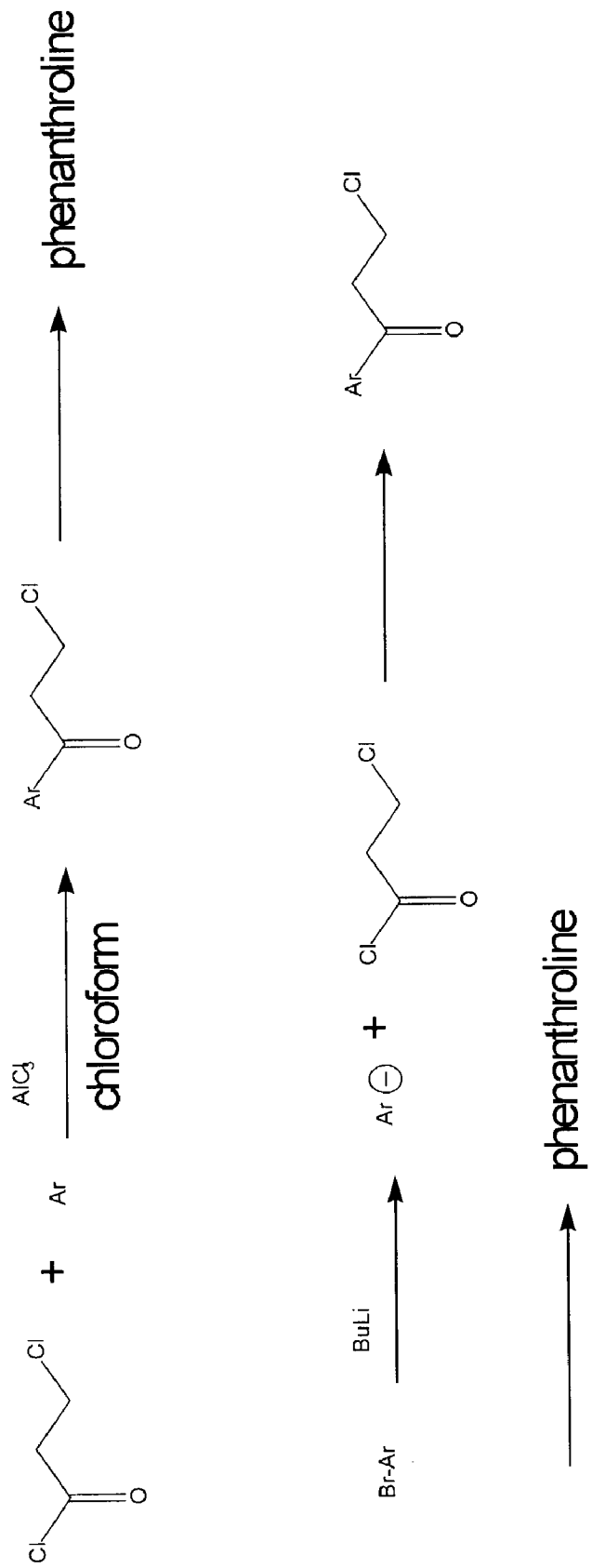
FIG. 9 is a synthetic scheme for the preparation of 3-chloropropioaromatic ketones useful in making phenanthrolines for osmium compounds of the invention.

A synthetic scheme for the preparation of 3-chloropropioaromatic ketones useful in making phenanthrolines for osmium complexes of the invention is shown in FIG. 9.

Figure 10:
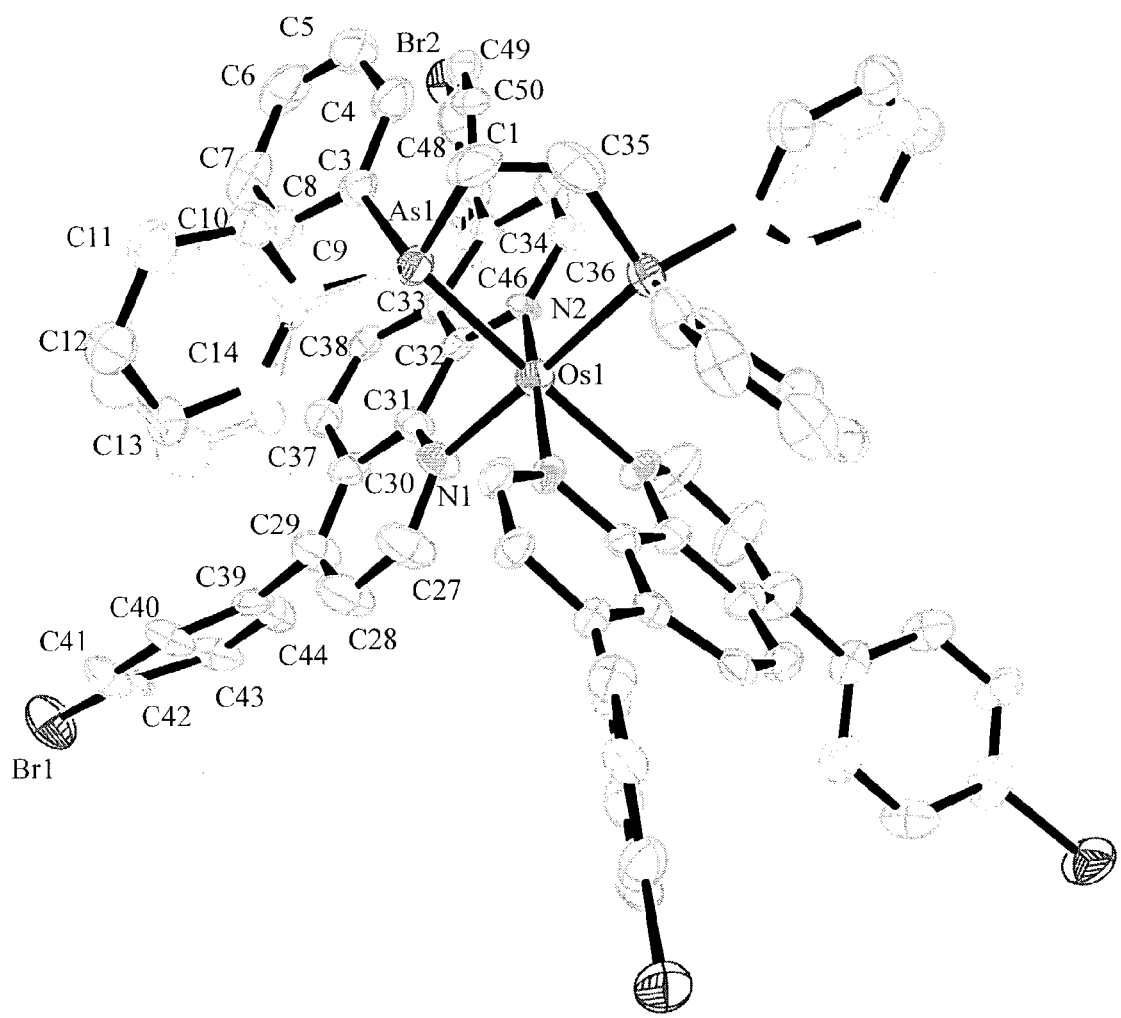
FIG. 10 is a three-dimensional molecular structure of a representative osmium complex of the invention.

A three-dimensional molecular structure of a representative osmium complex (Complex 12) of the invention is shown in FIG. 10.

FIG. 11 is a table summarizing the optical properties for representative osmium complexes of the invention: absorption maxima for various ligand and charge transfer bands (nm); extinction coefficient ($\epsilon$); emission wavelength maxima (nm); luminescence lifetime ($\tau$, ns); and luminescence quantum yield ($\Phi$).

Complexes with bipyridyl ligands exhibit an absorption band at >300 nm, while complexes with phenanthroline ligands exhibit an absorption band at <290 nm. These bands are attributed to the $\pi$-$\pi^*$ transition centered on the ligand. These ligand $\pi$-$\pi^*$ transition bands exhibit the strongest $\epsilon$ that is >60,000 L·$cm^{-1}$·$mol^{-1}$. Absorption bands that occur at roughly 390 and 500 nm are the $^1$MLCT and spin-forbidden $^3$MLCT bands. These are weaker bands with $\epsilon$ of 16,000 and 3700 L·$cm^{-1}$·$mol^{-1}$ for complex 1. Extending the conjugation length of the polypyridyl ligand increases the strength of all absorption bands. Complexes 1, 2, and 3 are based upon ligand 21. These have $\epsilon$ of 17,000 L·$cm^{-1}$·$mol^{-1}$ for the $^1$MLCT, 5000 L·$cm^{-1}$·$mol^{-1}$ for $^3$MLCT, and 70,000 L·$cm^{-1}$·$mol^{-1}$ for the LC state. Additional substitution or extending the conjugation length as in complexes 4, 5, and 6 affords $\epsilon$ of 28,000 L·$cm^{-1}$·$mol^{-1}$ for the $^1$MLCT, 11,000$\epsilon$ for the $^3$MLCT, and 91,000 L·$cm^{-1}$·$mol^{-1}$ for the LC state. The same trends were observed for the phenanthroline-containing complexes (7, 8 versus 13, 14). With the extended conjugation in these systems, additional LC bands were observed between the main polypyridyl LC peak and the $^1$MLCT transition.

At room temperature the complexes feature smooth, unstructured exponential Gaussian emission typical of MLCT emission. The emission of the arsine complexes is to the red of the emission of the phosphine complexes. This offers the ability to tune the emission of Os(II) complexes by the use of different ligands to the specific application. Emission lifetime for the bipyridyl complexes (1-6) were observed at roughly 450 ns, while the lifetimes for the phenanthroline complexes (7-14) were 1.2-2.0 µs. The difference in lifetime between the bipyridine- and phenanthroline-containing complexes may be due to the extended ring system of the phenanthroline. The complexes with arsine ligands (23, 25) had shorter emission lifetimes than those with phosphine ligands (24). This may be due to the fact that arsenic is a heavier atom than phosphorus, thus increasing the rate of intersystem crossing and rate of phosphorescence. There was some effect of extending the conjugation length on the outer portion of the polypyridyl ligands and emission lifetime, as complexes with extended $\pi$ systems (5, 6, 13, and 14) had slightly shorter emission lifetimes. The large spin-orbit coupling constant of osmium (~3500 $cm^{-1}$), and strong back-bonding between ligand and metal is resulting in short emission lifetime of the complexes with minor contributions from the arsenic, phosphorus, and the extended π system. Complex 11 was the most efficient photoluminescence emitter with 45% quantum yield (Φ), which is given by the following expression:

$$\Phi = \frac{k_p}{k_p + k_{nr} + k_q[Q]} \quad (1)$$

where $k_p$ is the rate of radiative decay, $k_{nr}$ is the nonradiative decay rate, and $k_q$ is the quenching rate. A common quencher of luminescence is oxygen.

The 1,10-phenanthroline complexes had quantum yields in excess of 30%. The complexes with ligand 25 in general have greater quantum yields than the complexes with ligand 24. This may be due to the heavy atom effect. From the lifetime data, complexes with arsine ligands have shorter lifetimes than complexes with phosphine ligands. The heavier arsenic increases spin-orbit coupling, which increases the rate of intersystem crossing. This may have the effect of making $k_p$ more competitive with $k_{nr}$ (eq 2) in the arsine complexes, thus increasing quantum yields of the complexes with ligand 25. Osmium(II) complexes have been reported with quantum yields up to 24% in the literature. The reported complexes are based upon ligand 24 and other non-phenyl-substituted bipyridyl ligands. The complexes have a reported emission at 600 nm. The significantly red-shifted complexes (630-640 nm) have significantly greater quantum yields in seeming defiance of the energy gap law. The use of phenyl derivatives of 2,2'-bipyridyls and 1,10-phenanthrolines has been shown to increase quantum yields. The radiative and nonradiative rate terms in the quantum efficiencies of Ru(II) complexes has also been discussed before. An explanation of this phenomenon may be the reduction of bond vibrations and rotations that quench luminescence. C—H, N—H, and O—H bond vibrations and C—C bond rotations are well-known to quench luminescence. The increase in quantum yield by reduction in C—H bond vibrations is observable where complexes based upon ligand 23 (complexes 1, 5, and 9) have significantly weaker quantum yield than similar complexes based upon ligand 25 (complexes 3, 6, and 11). In the crystal structures given for complexes 3 and 12, the phenyl groups are rotated out of the plane of the main polypyridyl structure. It has been shown that phenyl groups on polypyridyl complexes become coplanar with the main polypyridyl structure in the excited state. This extends the π-system of the ligand, which hinders C—C bond rotation in the excited state. Thus, the use of phenyl groups reduces pathways (such as C—H bond vibration and C—C bond rotation) of nonradiative deactivation of the excited state.

Green-Emitting Osmium Complexes. In another embodiment of the invention, green-emitting osmium complexes are provided. These osmium complexes have the formula: [Os (II)N—N(L—L)'$]^{2+}$ 2A$^-$ (or A$^{2-}$), where N—N is a Substituted or Unsubstituted bipyridine or phenanthroline ligand, L—L is a strong π-acid ligand, and A is either a singly or doubly negatively charged counter ion.

In one embodiment, the osmium complex includes one bipyridine ligand, two π-acid bidentate ligands, and one or two counter ions. In another embodiment, the osmium complex includes one phenanthroline ligand, two π-acid bidentate ligand, and one or two counter ions. The bipyridine ligand, the phenanthroline ligand, the π-acid bidentate ligand, and counter ions can be as described above for the red-emitting complexes.

The emission of osmium complexes can be tuned by limiting the number of bipyridine or phenanthroline ligands. The backbonding orbitals on the π-acid ligands (e.g., arsine and phosphine ligands) are very high in energy, thus the charge transfer manifold does not take place through those ligands. By limiting the number of bipyridine or phenanthroline ligands, the number of accepting orbitals is limited. Three phenanthroline ligands coordinated to osmium (II) provides a complex with infrared emission, and two coordinated phenanthroline ligands provides a complex with red emission. Therefore, by limiting the number of bipyridine or phenanthroline ligands to a single ligand, complexes that emit other colors, such as yellow and green, can be provided. Thus, in another embodiment, the invention provides green-emitting osmium complexes.

The preparation of representative green-emitting osmium complexes is described in Example 9.

The absorbance and emission properties of representative green-emitting osmium complexes are summarized in Table 3 (absorption maxima for various ligand and charge transfer bands (nm); extinction coefficient (ε); emission wavelength maxima (nm); luminescence lifetime (τ, ns); and luminescence quantum yield (Φ)).

TABLE 3

Optical Properties for Representative Osmium Complexes.

| Os Complex | LC (nm) (ε) | Emission (nm) | τ (ns) | Φ |
|---|---|---|---|---|
| Os(dppene)$_2$phen | 289 (29000) | 520 | 2100 | 0.60 |
| Os(dpaene)$_2$phen | 286 (28000) | 570 | 1800 | 0.50 |

In Table 3, Os(dppene)$_2$phen refers to: [osmium (II) (1,10-phenanthroline) bis(cis-1,2-vinylenebis(diphenylphosphine))]$^{2+}$ (hexafluorophosphate)$_2$, and Os(dpaene)$_2$phen refers to [osmium (II) (1,10-phenanthroline) bis(cis-1,2-vinylenebis(diphenylarsine))]$^{2+}$ (hexafluorophosphate)$_2$.

The performance properties (voltage needed for 1 cd/m$^2$ brightness (V$_1$, V), maximum brightness (B$_{max}$, cd/m$^2$), and maximum external quantum efficiency (η$_{max}$)) for a representative LED doped with green-emitting osmium complexes of the invention are summarized in Table 4: ITO//BTPD-PFCB//Os complex/PVK:PBD//Ca (Type I).

TABLE 4

Performance Properties for LED: Green-Emitting Osmium Complexes.

| Os Complex | Device | V$_1$(V) | B$_{max}$(cd/m$^2$) | η$_{max}$ |
|---|---|---|---|---|
| Os(dppene)$_2$phen | I | 7.0 | 765 | 0.083 |
| Os(dpaene)$_2$phen | I | 7.0 | 1125 | 0.11 |

The green osmium complexes have much lower brightness and efficiency than their red-emitting counterparts. From the absorbance data it can be seen that the charge transfer absorption bands are both weaker and blue shifted by greater than 100 nm from the red-emitting complexes. This means that there is virtually no overlap with the PVK host material and what overlap there is has very little cross-section. Thus, there is no energy transfer from the host to the dopant. The loss in efficiency also leads to the conclusion that the complexes' ability to charge trap both holes and electrons which could be attributed to the reduction of the π system of these complexes.

In another aspect, the present invention provides light-emitting devices that include the osmium complexes.

The osmium compounds described herein can be used as emitters in organic light emitting devices. Accordingly, the compounds can be present in an emissive layer (i.e., a layer from which light is primarily emitted) of a such device. The emissive layer can be a layer that includes one or more osmium complexes of the invention. The osmium complexes can also be present as dopants. For example, an emissive layer can include host material doped with one or more osmium complexes. The host material can include any compound, including organic and organometallic compounds, suitable for an emissive layer in an OLED. Exemplary organic host materials include BCP (bathocuproine or 2,9-dimethyl-4,7-diphenyl-1,10-phenanthroline), CBP (4,4'-N,N'-dicarbazole biphenyl), OXD7 (1,3-bis(N,N-t-butylphenyl)-1,3,4-oxadiazole), TAZ (3-phenyl-4-(1'-naphthyl)-5-phenyl-1,2,4-triazole), NPD (4,4'-bis[N-(1-naphthyl)-N-phenyl-amino]biphenyl). Other host material can include CuPc (copper phthalocyanine), $Alq_3$ (aluminum tris(8-hydroxyquinolate)), $BAlq$ ((1,1'-biphenyl)-4-olato)bis(2-methyl-8-quinolinolato N1,O8)aluminum). Other materials that can be included in an emissive layer, in addition to the osmium complexes, include Irppy (tris(2-phenylpyridinato-N,C2')iridium(III)), FIrpic (bis(2-(4,6-difluorophenyl)-pyridinato-N,C2')iridium(III) (picolinate)), and other metal complexes. As dopants, the present compounds can be present in the emissive layer, such as in host material, in amounts of from about 1 to about 20 percent by weight, from about 5 to about 15 percent by weight, from about 5 to about 10 percent by weight based on the total weight materials in the layer.

In one embodiment, the osmium complexes are included in a light-emitting device in a host material. Suitable host materials include those having spectral overlap between host emission and osmium complex absorbance so as to effect efficient Forster energy transfer from the host to the emitter. Suitable hosts include blends of poly(N-vinylcarbazole) and 2-t-butylphenyl-5-biphenyl-1,3,4-oxadiazole (PVK:PBD), blends of poly(2-vinylnaphthalene) and 2-t-butylphenyl-5-biphenyl-1,3,4-oxadiazole (PVN:PBD), and poly(fluorene) (PF) and its derivatives. For these blends the ratio of each component can be varied. In one embodiment, the PVK:PBD blend is a 70:30 blend. In one embodiment, the PVN:PBD blend is a 70:30 blend.

The amount of osmium complex in the host can also be varied. In one embodiment, the amount of osmium complex present in the host is sufficient to quench the emission of the host. The amount of osmium complex in the host can range from about 1 to about 15 percent by weight of the host. In one embodiment, the osmium complex is present in the range from about 2 to about 5 percent by weight of the host. In another embodiment, the osmium complex is present in about 3 percent by weight of the host.

Accordingly, the present invention includes compositions comprising compounds of the present invention. In some embodiments, the compositions include at least one osmium complex of the invention and another compound or material suitable for use in an OLED. As noted above, other compounds or materials can include any of the host materials mentioned above as well as other emitters or metal complexes.

Devices comprising the present compounds have advantageous properties as compared with known devices. High external quantum and luminous efficiencies can be achieved in the present devices. Device lifetimes are also generally better than, or at least comparable to, some of the most stable fluorescent devices reported.

As noted above, depending on the osmium complex, the devices of the present invention can emit red or green. In some embodiments, the devices can have external quantum efficiencies greater than about 4%, 5%, 6%, 7%, 8%, 10%, 12%, or higher at a brightness greater than about 10, 100, 1000 $cd/m^2$, or more.

Typical devices are structured so that one or more layers are sandwiched between a hole injecting anode layer and an electron injecting cathode layer. The sandwiched layers have two sides, one facing the anode and the other facing the cathode. Layers are generally deposited on a substrate, such as glass, on which either the anode layer or the cathode layer may reside. In some embodiments, the anode layer is in contact with the substrate. In some embodiments, for example when the substrate comprises a conductive or semiconductive material, an insulating material can be inserted between the electrode layer and the substrate. Typical substrate materials, that may be rigid, flexible, transparent, or opaque, include glass, polymers, quartz, sapphire, and the like.

In some embodiments, devices of the invention include layers in addition to a layer comprising the present compounds (e.g., an emissive layer). For example, in addition to the electrodes, devices can include any one or more hole blocking layers, electron blocking layers, exciton blocking layers, hole transporting layers, electron transporting layers, hole injection layers, or electron injection layers. Anodes can include an oxide material such as indium-tin oxide (ITO), $Zn$—$In$—$SnO_2$, $SbO_2$, or the like, and cathodes can include a metal layer such as Mg, Mg:Ag, or LiF:Al. Among other materials, the hole transporting layer (HTL) can include triaryl amines or metal complexes. Similarly, the electron transporting layer (ETL) can include, for example, aluminum tris (8-hydroxyquinolate) ($Alq_3$) or other suitable materials. A hole injection layer can include, for example, 4,4',4"-tris(3-methylphenylphenylamino)triphenylamine (MTDATA), polymeric material such as poly(3,4-ethylenedioxythiophene) (PEDOT), or metal complex such as, for example, copper phthalocyanine (CuPc), or other suitable materials. Hole blocking, electron blocking, and exciton blocking layers can include, for example, BCP, BAlq, and other suitable materials such as FIrpic or other metal complexes. The osmium complexes of the invention can be included in any of the above mentioned layers.

Light emitting devices of the invention can be fabricated by a variety of techniques well known to those skilled in the art. Small molecule layers, including those comprised of neutral metal complexes, can be prepared by vacuum deposition, organic vapor phase deposition (OVPD), or solution processing such as spin coating. Polymeric films can be deposited by spin coating and chemical vapor deposition (CVD). Layers of charged compounds, such as salts of charged metal complexes, can be prepared by solution methods such a spin coating or by an OVPD method such as disclosed in U.S. Pat. No. 5,554,220, expressly incorporated herein by reference in its entirety. Layer deposition generally, although not necessarily, proceeds in the direction of the anode to the cathode, and the anode typically rests on a substrate. Devices and techniques for their fabrication are described throughout the literature and in, for example, U.S. Pat. Nos. 5,703,436; 5,986,401; 6,013,982; 6,097,147; and 6,166,489, each expressly incorporated herein by reference in its entirety. For devices from which light emission is directed substantially out of the bottom of the device (i.e., substrate side), a transparent anode material such as ITO may be used as the bottom electron. Because the top electrode of such a device does not need to be transparent, such a top electrode, which is typically a cathode, may be comprised of a thick and reflective metal layer having a high electrical conductivity. In contrast, for transparent or top-emitting devices, a transparent cathode may be used such as disclosed in U.S. Pat. Nos. 5,703,436 and 5,707,745, each expressly incorporated herein by reference in its entirety. Top-emitting devices may have an opaque and/or reflective substrate, such that light is produced substantially out of the top of the device. Devices can also be fully transparent, emitting from both top and bottom.

Transparent cathodes, such as those used in top-emitting devices preferably have optical transmission characteristics such that the device has an optical transmission of at least about 50%, although lower optical transmissions can be used. In some embodiments, devices include transparent cathodes having optical characteristics that permit the devices to have optical transmissions of at least about 70%, 85%, or more. Transparent cathodes, such as those described in U.S. Pat. Nos. 5,703,436 and 5,707,745, typically include a thin layer of metal such as Mg:Ag with a thickness, for example, that is less than about 100 Angstrom. The Mg:Ag layer can be coated with a transparent, electrically-conductive, sputter-deposited, ITO layer. Such cathodes are often referred to as compound cathodes or as TOLED (transparent-OLED) cathodes. The thickness of the Mg:Ag and ITO layers in compound cathodes may each be adjusted to produce the desired combination of both high optical transmission and high electrical conductivity, for example, an electrical conductivity as reflected by an overall cathode resistivity of about 30 to 100 ohms. However, even though such a relatively low resistivity can be acceptable for certain types of applications, such a resistivity can still be somewhat too high for passive matrix array OLED pixels in which the current that powers each pixel needs to be conducted across the entire array through the narrow strips of the compound cathode.

Light emitting devices of the present invention can be used in a pixel for an electronic display. Virtually any type of electronic display can incorporate the present devices. Displays can include computer monitors, televisions, personal digital assistants, printers, instrument panels, bill boards, and the like. In particular, the present devices can be used in flat panel displays and heads-up displays.

In one embodiment, the device is a single-layer device. In other embodiments, the device includes more than one layer, for example, a double-layer device or a triple-layer device. Representative devices of the invention are illustrated in FIGS. 13A-13C.

Figure 13A:
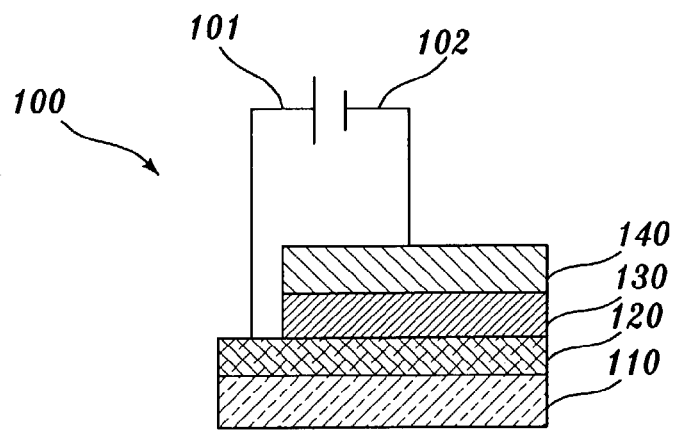
FIGS. 13A-13C illustrate representative organic light-emitting devices of the invention.

A single layer device (an electroluminescent cell) is illustrated in FIG. 13A. Referring to FIG. 13A, representative device 100 includes first substrate layer 110, indium-tin oxide (ITO) anode layer 120, emissive layer 130, electron transporting and protective layer 140, anode 101, and cathode 102. In the device, the first substrate layer can be a glass substrate layer, and the electron transporting/protective layer can be a layer that includes gold. The emissive layer includes at least one osmium complex of the invention. The electroluminescent cell includes no polymer host. The emissive layer of this device includes the complex without a host.

Figure 13B:
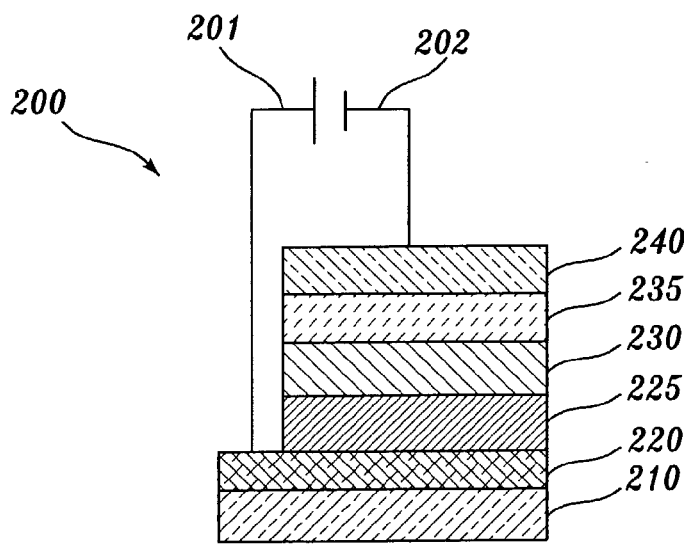

A double layer device is illustrated in FIG. 13B. Referring to FIG. 13B, representative device 200 includes first substrate layer 210, indium-tin oxide (ITO) anode layer 220, hole-transporting material layer 225, emissive layer 230, electron injection cathode layer 235, protective layer 240, anode 201, and cathode 202. In the device, the first substrate layer can be a glass substrate layer, and the protective layer can include aluminum, gold, or silver. The emissive layer includes at least one osmium complex of the invention and, optionally, a host material such as a blend of poly(N vinylcarbazole) and 2-t-butylphenyl-5-biphenyl-1,3,4-oxadiazole (PVK:PBD). The hole-transporting layer can include a tetraphenyldiaminobiphenyl-containing perfluorocyclobutane polymer (BTPD-PFCB) prepared by the thermal polymerization of a bis-tetraphenyldiaminobiphenyl (BTPD)-containing bis-trifluorovinylether monomer to provide a perfluorocyclobutane (PFCB) polymer. The electron injection cathode layer can include calcium. Thus, in one embodiment, the invention provides a double layer device having a hole-transport layer, an emissive layer that includes an osmium complex as described above, and an electron injection cathode layer.

Figure 13C:
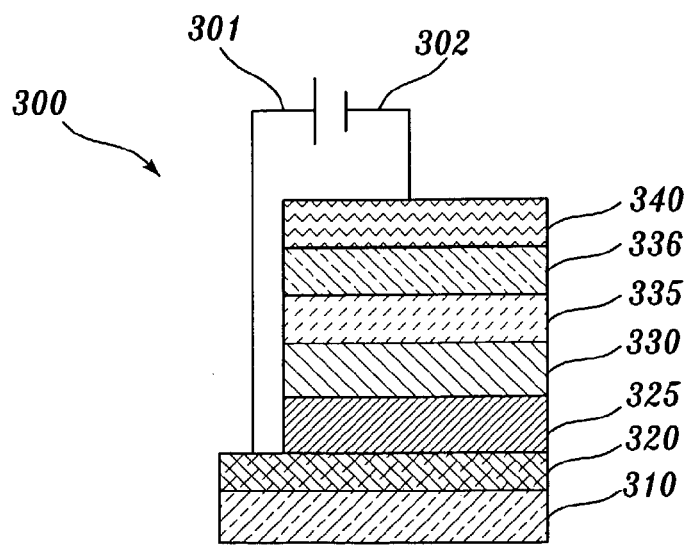

A triple layer device is illustrated in FIG. 13C. Referring to FIG. 13C, representative device 300 includes first substrate layer 310, indium-tin oxide (ITO) anode layer 320, hole-transporting material layer 325, emissive layer 330, electron transporting layer 335, electron injection cathode layer 336, protective layer 340, anode 301 and cathode 302. In the device, the first substrate layer can be a glass substrate layer, and the protective layer can include aluminum, silver, or gold. The emissive layer includes at least one osmium complex of the invention and, optionally, a host material such as PVK:PBD. The hole-transporting layer can include BTPD-PFCB. The electron transporting layer can include aluminum tris(8-hydroxyquinolate) ($Alq_3$), and the electron injection cathode layer can include lithium fluoride. Thus, in one embodiment, the invention provides a double layer device having a hole-transport layer, an emissive layer that includes an osmium complex as described above, an electron transporting layer, and an electron injection cathode layer.

The fabrication of a representative device of the invention is described in Example 10. Performance of representative devices is summarized in Table 2, FIG. 12. Table 2 compares the performance properties for LEDs doped with representative osmium complexes of the invention with either PVK:PBD or PVN:PBD as host material for a representative double layer device: ITO//BTPD-PFCB//Os complex/PVK:PBD (about 45 nm thickness)//Ca (Type I); or ITO//BTPD-PFCB//Os complex/PVN:PBD (about 45 nm thickness)//Ca (Type II). Table 2 summarizes the voltage needed for 1 cd/m$^2$ brightness ($V_1$, V); maximum brightness ($B_{max}$, cd/m$^2$); and maximum external quantum efficiency ($\eta_{max}$) for representative double layer devices. In Table 2, osmium complex counter ion is X$^-$: "HFB" refers to heptafluorobutylate; "Ts" refers to tosylate (i.e., p-methyl sulfonate); "Tf" refers to triflate (i.e., p-trifluoromethyl sulfonate); and "PF$_6$" refers to hexafluorophosphate.

The osmium complexes demonstrate good phosphorescence efficiency and short excited-state lifetime, which are very desirable properties for light-emitting diode applications. To study the device performances of these complexes, double-layer devices were fabricated by doping the osmium complexes at a weight ratio of 3 wt % into PVK:PBD or PVN:PBD blends. BTPD-PFCB was used as the hole-transporting layer. At the doping level of 3 wt %, the EL spectra of the devices are almost identical to the PL spectra of the osmium complexes. No emission from the host materials was observed. Table 2 summarizes the performance of the devices. As can be seen, even with a simple double-layer structure and PVK:PBD as the host (type I devices), relatively good performances can be achieved. Among type I devices, the best external quantum efficiency of 0.78% was obtained from complex 11 with Ts as the counter ion, while the highest brightness of 1430 cd/m$^2$ was obtained from complex 10 with Ts as the counter ion. In general, the complexes utilizing arsine ligand 25 have better quantum yields than those with ligand 24. Interestingly, the device efficiency follows this trend. It has been found that the osmium complexes trap both electrons and holes, which facilitates the direct recombination of holes and electrons on the complex sites and benefits the device efficiency. It should be noted that the counter ion used in the complexes also affects the device performance, presumably through affecting the charge trap/transport property of the complex, thereby providing an additional way of tuning the device properties. Better external quantum efficiencies were achieved from type II devices, where PVN:PBD was used as the host and excitation was transferred from the host more efficiently to the Os complex dopants, presumably through a Forster mechanism. Compared with the EL emission of PVK:PBD host, the EL emission of PVN:PBD host peaks at shorter wavelength and provides a much better spectral overlap with the absorption spectra of the osmium complexes. In Forster energy transfer, the energy transfer rate is proportional to the integral of the spectral overlap between the emission of the energy donor and the absorption of the energy acceptor. Therefore, PVN:PBD can transfer energy more efficiently to the osmium complexes. Consequently, devices with a PVN:PBD host are more efficient than devices with a PVK:PBD host. It is very interesting to further compare the performance of 2 and 14 doped type II devices. The maximum efficiency of a complex 14 doped PVN:PBD device is 2.2%, corresponding to a photometric efficiency of 1.9 cd/A, while that of a complex 12 doped PVN:PBD device is 0.79%. Substitution of bromide in complex 12 with a naphthyl group in complex 14 almost doubles the extinction coefficient of $^1$MLCT absorption of the osmium complex (see Table 2). A larger extinction coefficient contributes to a larger spectral overlap integral between the emission spectrum of PVN:PBD host and the absorption of complex 14. This also contributes to a more efficient energy transfer from PVN:PBD to complex -14. However, compared to the devices based on PVN:PBD, the devices based on PVK:PBD have a lower turn-on voltage and higher brightness, mainly due to the better hole transport property of PVK. Nevertheless, the device data clearly demonstrate that osmium complexes, when carefully designed, are candidates for light emitting device applications.

OLEDs have been reported for ruthenium complexes with similar emission profiles to the osmium complexes of the invention. Various polymer host devices with emissions between 611 and 665 nm gave brightness in the range of 200-650 cd/m$^2$ and efficiency in the range of 0.08-2.5%. In comparison, the osmium complex-containing devices have efficiencies up to 2.2% with a brightness of 870 cd/m$^2$ at 637 nm emission, or brightness of 1210 cd/m$^2$ with efficiency of 0.78% at 629 nm emission. The reported ruthenium complexes have emission quantum yields of 3.6-6.2%, significantly less than the osmium complexes. At 611 nm emission we report a device with brightness of over 1400 cd/m$^2$ and efficiency of 0.48%.

In one aspect, the invention provides red-emitting osmium complexes that are useful in light-emitting applications. These complexes feature strong MLCT absorption bands in the visible region and strong red phosphorescent emission ranging from 611 to 651 nm, with quantum yields up to 45%. The electronic structure and emission properties of the osmium complexes can be modified by changing the ligand structures. Electrophosphorescent devices are provided that include the osmium complexes with doped PVK:PBD or PVN:PBD as the emitting layer. When PVK:PBD was used as the host matrix, brightness of over 1400 cd/m$^2$ was achieved. The best external quantum efficiency of 2.2%, which corresponds to a photometric efficiency of 1.9 cd/A, was achieved when PVN:PBD was used as the host matrix. It was found that the counter ion also affects the performance of the complexes and devices, providing an additional way of tuning the material and device properties.

The following examples are provided for the purpose of illustrating, not limiting, the invention.

EXAMPLES

Example 1

General Methods for Osmium Complex Characterization

Elemental analyses were carried out by Oneida Research Services, Inc., Whitesboro, N.Y. UV-Vis absorption spectra were measured on a Shimadzu UV-1601 spectrophotometer. Quantitative measurements were obtained by using 1.000 cm path length quartz cells with absolute ethanol as the solvent. Electrospray mass spectroscopy was measured on either an Esquire-LC ion trap mass spectrometer (Bruker and Hewlett-Packard) or an Applied Biosystems Mariner ESI-TOF mass spectrometer. $^1$H NMR was carried out on a 200 MHz Bruker FT-NMR spectrometer.

Emission spectra of ethanol solutions were collected on a Perkin-Elmer LS50B fluorescence spectrophotometer. The wavelength sensitivity of the instrument was calibrated prior to measurements using a standard 20 W tungsten lamp of known output. All emission spectra were corrected to the calibration curve calculated from the known lamp output. The solutions were degassed using argon for 30 min before the measurement. Photoluminescence (PL) quantum yields to ±10% of the osmium complexes ($\Phi_{Os}$) in ethanol solutions were obtained with Ru(II) tris(bathophenanthroline) dichloride as the standard, which has a known quantum yield of 0.366, from the following equation:

$$\Phi_{Os} = \frac{\text{abs } Ru}{\text{area } Ru} \frac{\text{area } Os}{\text{abs } Os} \times 36.6\% \quad (2)$$

where abs is the absorbance of the sample and area is the integration of the emission curve. Samples were excited through the LC state at 280 nm with absorption of 0.050. Temperature for the measurements was 25±2° C.

For lifetime measurement, the osmium complexes were dissolved into a paint solution of FIB7 polymer and trifluorotoluene. FIB7 is a very photostable polymer and does not absorb light above 235 nm. The solution was spray-painted onto a polished aluminum plate and dried at 50° C. The samples were put into a sample holder, placed under vacuum, and excited at 338 nm with a nitrogen pulse laser. The luminescence decay was monitored and the lifetime was calculated. Samples for photodegradation and temperature dependence were prepared following the same procedures as for the lifetime measurements detailed above. A tungsten-halogen lamp filtered by a FIV-026 band-pass filter was used as the excitation source (400 nm, FWHM=20 nm). The power density was 925 µW cm$^{-2}$. The emission intensity was monitored with a photomultiplier tube. The illumination for degradation was continuous and the temperature was set to 25° C., while for temperature dependence the shutter time was 1 s and the temperature ranged from 5 to 50° C.

Example 2

The Preparation of a Representative Bidentate Ligand (L—L): cis-1,2-Vinylenebis(diphenylarsine)

In this example, the synthesis of a bidentate ligand (L—L), cis-1,2-vinylenebis(diphenylarsine), useful in making the complexes of the invention is described.

Diphenylarsine (Organometalics, 25.00 g, 108.6 mmol) was used as received and added to 400 mL of freshly dried (sodium/benzophenone) THF. The solution was stirred under nitrogen and cooled to −78° C. using an acetone/dry ice bath. To this solution was added n-butyl lithium (1.6 M in hexane, 1.05 eq, 114.1 mmol). The solution was allowed to stir for 1 h. The acetone bath was then removed and cis-dichloroethylene (TCI-America, 10.66 g, 110.0 mmol) was added. The solution was allowed to slowly warm to 18.5° C. and react overnight. Water was added and the THF was removed by rotary evaporation under vacuum at 40° C. The water was removed by filtration and the solid material was washed with large amounts of de-ionized water. The sample was dried under vacuum and then recrystallized three times from butanol. Yield: 23.97 g (91%). $^1$H NMR (DMSO): 7.63 (s, 2H), 7.35 (20H). Elemental analysis, calculated: C, 64.48%; H, 4.58%. found: C, 64.10%; H, 4.28%.

Example 3

The Preparation of a Representative Bipyridine Ligand (N—N): 4,4'-Bis(p-biphenyl)-2,2'-bipyridine In this example, the synthesis of a bipyridine ligand (N—N), 4,4'-bis(p-biphenyl)-2,2'-bipyridine, useful in making the complexes of the invention is described. The procedure was an adaptation and combination of the methods reported by Haginiwa and Chase.

4,4'-Dibromo-2,2'-bipyridine (2.000 g, 6.37 mmol) and biphenyl-4-boronic acid neopentyl glycol ester (4.238 g, 15.92 mmol) were dissolved into 80 mL DMF (Aldrich). The solution was stirred for 1 h under nitrogen and tetrakis(triphenylphosphine) Pd(0) (0.191 mmol) was added. The solution was heated to 60° C. and 10 mL deoxygenated saturated potassium carbonate aqueous solution was added drop wise over a period of 5 min. The solution was then warmed to 85-95° C. The coupling was allowed to proceed under these conditions for 24 h. The solution was warmed to 115° C. and the reaction was allowed to proceed for an additional 5 h. The solution was cooled to room temperature and poured into 500 mL of 0.25 M KOH solution. The precipitate was collected by vacuum filtration and washed with water, allowed to dry, and then washed with methylene chloride. The methylene chloride layer was a dark brown while the precipitate was a light gray which gave a mass of 461. The gray powder was suspended into 250 mL of xylene (Fisher Scientific) and refluxed for 10 minutes and filtered. Small colorless crystals (150 mg) of 4,4'-bis(p-biphenyl)-2,2'-bipyridine formed in the mother liquid. This process was repeated 10 times to yield 1.5 g of material (51%, remainder is the mono-substituted material, which was soluble in organic solvents such as methylene chloride). 4,4'-Bis(p-biphenyl)-2,2'-bipyridine was very insoluble in organic solvents at room temperature. $^1$H NMR (CDCl$_3$) as a Ru(II) HFB$_2$ complex: 9.08 (d, 6H), 7.97 (m, 18H), 7.80 (m, 18H), 7.61 (m, 12H), 7.45 (m, 18H). Mass spectrometry (m/z): 461.6. Elemental analysis, calculated: C, 88.67; H, 5.25; N, 6.08, found C, 89.06; H, 5.32; N, 6.21.

The procedure described above was modified to provide the following compound.

4,4'-Bis(diphenylether)-2,2'-bipyridine. Yield 0.95 g (30.4%). $^1$H NMR (DMSO-d$_6$): 8.750 (d, 2H), 8.631 (m, 4H), 7.904 (m, 4H), 7.800 (m, 4H), 7.459 (t, 2H), 7.147 (m, 8H). Mass spectroscopy (m/z): 493.2. Elemental analysis, calculated: C, 82.91; H, 4.91; N, 5.69, found: C, 83.09; H, 4.99; N, 5.77.

Example 4

The Preparation of a Representative Phenanthroline Ligand (N—N): 4,7-Bis(p-bromophenyl)-1,10-phenanthroline In this example, the synthesis of a phenanthroline ligand (N—N), 4,7-bis(p-bromophenyl)-1,10-phenanthroline, useful in making the complexes of the invention is described.

o-Nitroaminobenzene (15.00 g, 0.108 mmol), arsenic acid (60.00 g, 0.156 mmol), and o-phosphoric acid (180 mL) were added to a round bottom flask with stir bar and purged with nitrogen. The solution was heated to 100° C. and a melt of p-bromo-3-chloropropriophenone (37.128 g, 150 mmol), was added dropwise while maintaining the solution at 100° C. The solution was heated to 140-150° C. for 1.5 hours and then cooled to 80° C. and poured onto ice. The solution was then brought to pH 12 with K$_2$CO$_3$ and the organics were extracted from the aqueous phase using methylene chloride. The contents were purified on basic alumina (methylene chloride) to yield 30 g (91.1 mmol) of 4-(4-bromophenyl)-8-nitroquinoline.

4-(4-Bromophenyl)-8-nitroquinoline (30 g, 91.1 mmol) was added to absolute ethanol (120 mL) and purged with nitrogen. To this was added tin (II) chloride (190 mmol) and the reaction mixture refluxed for 4 hours. The pH was adjusted to 12 with aqueous NaOH and the organics were extracted using methylene chloride. The organics were then purified on basic alumina (methylene chloride/methanol 99:1) to yield 21.2 g of 4-(4-bromophenyl)quinolin-8-yl amine.

4-(4-Bromophenyl)quinolin-8-yl amine (20 g, 66.9 mmol), arsenic acid (26.88 g, 70 mmol), and o-phosphoric acid (80 mL) were heated to 100° C. under nitrogen. To this reaction mixture was added a melt of 25 g of p-bromo-3-chloropropriophenone (101 mmol) dropwise. The solution was then heated to 140-150° C. and solidified as 4,7-bis(p-bromophenyl)-1,10-phenanthroline was formed. The solid was extracted and brought to a pH of 12 and extracted with chloroform. The solid product was recrystallized from DMF to yield 22.03 g of 4,7-bis(p-bromophenyl)-1,10-phenanthroline.

The following phenanthroline derivatives (ligands N—N) were synthesized from 4,7-bis(p-bromophenyl)-1,10-phenanthroline by Suzuki cross coupling reaction.

4,7-Bis(4'-phenoxy-biphenyl-4-yl)-1,10-phenanthroline. Elemental analysis, calculated: C, 86.20; H, 4.82; N, 4.19; found: C, 86.32; H, 4.98; N, 4.28. $^1$HNMR (DMSO-d$_6$): 9.20 (d 2H), 8.88-7.65 (m 18H), 7.45 (t 4H), 7.25-7.06 (m 8H). Recrystallized from benzene to give a colorless crystalline solid.

4,7-Bis(4-naphthalen-2-yl-phenyl)-1,10-phenanthroline. Elemental analysis, calculated: C, 90.38; H, 4.83; N, 4.79; found: C, 90.45; H, 4.86; N, 4.81. $^1$HNMR (CDCl$_3$): 9.29 (d 2H), 8.14 (s 2H), 8.03-7.75 (m 14H), 7.72-7.63 (m 6H), 7.57-7.46 (m 4H). Recrystallized from DMF to give colorless crystalline solid.

Example 5

The Preparation of Representative Osmium Bipyridine Complexes

In this example, the synthesis of representative osmium bipyridine complexes of the invention, [Os(II) (N—N)$_2$L—L]$^{2+}$2A$^-$ (or A$^{2-}$), are described. A synthetic scheme for the preparation of representative osmium complexes having bipyridine ligands is illustrated in FIG. 6. FIG. 6 includes a key identifying the compound numbers (i.e., 1-6), bipyridine substituent (R), and bidentate ligand (L—L) by references number (i.e., 23-25).

Representative osmium complexes were prepared from osmium (II) bis(4,4'-diphenyl-2,2'-bipyridine) dichloride.

Osmium (II) bis(4,4'-diphenyl-2,2'-bipyridine) dichloride. Potassium hexachloroosmiate, (1 g, 2.078 mmol) and 4,4'-diphenyl-2,2'-bipyridine, (1.40 g, 4.54 mmol), were suspended in DMF (15 mL), purged with nitrogen for 1 h, and refluxed under a nitrogen atmosphere for 3 h. The solution was cooled to 18.5° C. and filtered. Much of the product, a mixture of [Os(4,4'-diphenyl-2,2'-bipyridine)$_2$Cl$_2$] and [Os(4,4'-diphenyl-2,2'-bipyridine)$_2$Cl$_2$]+precipitated out as it was only partially soluble in DMF (0.8 g of Os product per 60 mL DMF). Extractions were filtered through a fine frit and performed repeatedly until the filtrate, KCl, was only a light brown color. To a solution of 2 g of sodium dithionite (Alfa) in 400 mL cooled de-ionized water (0-3° C.) was added the DMF solution of the osmium complex dropwise. A dark purple precipitate of osmium (II) bis(4,4'-diphenyl-2,2'-bipyridine) dichloride formed instantly and was collected using vacuum filtration and washed repeatedly with water. This was done repeatedly with each extraction. Yield: 92%. The product complex had increased solubility and allowed the use of a silica flash column with methylene chloride mobile phase for purification.

The following osmium complexes of the invention were prepared from osmium (II) bis(4,4'-diphenyl-2,2'-bipyridine) dichloride prepared as described above.

Complex 1: [Osmium (II) bis(4,4'-diphenyl-2,2'-bipyridine) 1,2-bis(diphenylarseno)ethanel]$^{2+}$ X$_2$. Osmium bis(4,4'-diphenyl-2,2'-bipyridine) dichloride (0.5 g, 0.570 mmol) and ethylene bis(diphenylarsine) (Aldrich) (0.291 g, 0.600 mmol) were added to 10 mL of a mixture of 2-(2-ethoxyethoxy)ethanol and glycerol (75:25 by volume). The solution was purged with nitrogen for 1 h and then the solution was refluxed for 1.5 h. After cooling, the solution was added to water and the appropriate counter ion X (e.g., the sodium salt of heptafluorobutyrate, triflate, tosylate, or chloride) was added. The precipitate was collected by filtration, washed with water and dried under vacuum at 40° C. The dried precipitate was dissolved in methylene chloride (20 mL per g of complex) and precipitated with hexane. This was repeated three times to provide a bright red product. Yield: 90%. Mass spectrometry (m/2z): 647.1. Isotope Pattern: 645.1, 645.6, 646.1, 646.6, 647.1, 647.6, and 648.1. Fragmentation peak at m/2z=478.1 (m/2z−308−28), which corresponds to the fragmentation of a bipyridine ligand and the ethane bridge on the arsine. Elemental analysis, calculated: (heptafluorobutyrate counter ions). C, 54.49; H, 3.28; N, 3.26, found C, 54.65; H, 3.36; N, 3.30.

The above procedure was used in the synthesis of the following osmium complexes.

Complex 2: [Osmium (II) (4,4'-diphenyl-2,2'-bipyridine)$_2$ cis-1,2-bis(diphenylphosphino)ethylene]$^{2+}$ (heptafluorobutyrate)$_2$. Orange product. Yield: 85%. Mass spectrometry (m/2z): 602.7. Isotope pattern m/2z: 599.7, 600.2, 600.7, 601.2, 601.7, 602.2, 602.7, 603.2. Elemental analysis, calculated: C, 57.49%; H. 3.34%; N, 3.44%. Found: C, 58.00; H, 3.41; N, 3.33.

Complex 3: [Osmium (II) (4,4'-diphenyl-2,2'-bipyridine)$_2$ cis-1,2-vinylenebis(diphenylarsine)]$^{2+}$ (triflate)$_2$. Red product. Yield: 94%. Mass spectrometry (m/2z): 646.1. Isotope pattern (m/2z): 643.6, 644.1, 644.6, 645.1, 645.6, 646.1, 646.6, 647.1. Elemental analysis, calculated: C, 54.41%; H, 3.42%; N, 3.52%. Found C, 54.51; H, 3.48; N, 3.36. An absorption spectrum of this representative osmium complex with emission spectra as a function of excitation wavelength is shown in FIG. 7.

Complex 4: [Osmium (II) (4,4'-bis(p-diphenylether)-2,2'-bipyridine)$_2$ cis-1,2-vinylenebis(diphenylarsine)]$^{2+}$ (triflate)$_2$. Mass spectrometry (m/2z): 830.2. Isotope Pattern for 830.2 peak: 828.2, 828.7, 829.2 829.7, 830.2, 830.7, 831.2. Yield 90%. Elemental analysis, calculated: C, 58.89; H, 3.60; N, 2.86, found C, 59.01; H, 3.59; N, 2.88.

Complex 5: [Osmium (II) (4,4'-bis(p-biphenyl)-2,2'-bipyridine)$_2$ 1,2-bis(diphenylarseno)ethane]$^{2+}$ (heptafluorobutyrate)$_2$. Brick red product. Mass spectrometry (m/2z): 646.1. Isotope pattern (m/2z): 643.6, 644.1, 644.6, 645.1, 645.6, 646.1, 646.6, 647.1. Elemental analysis, calculated: C, 60.54; H, 3.59; N, 2.77, found C, 59.92; H, 3.34; N, 2.70.

Complex 6: [Osmium (II) (4,4'-bis(p-biphenyl)-2,2'-bipyridine)$_2$ cis-1,2-vinylenebis(diphenylarsine)]$^{2+}$ (triflate)$_2$. Mass spectrometry (m/2z): 798.2. Isotope pattern (m/2z): 795.7, 796.2, 796.7, 797.2, 797.7, 798.2, 798.7, and 799.2. Elemental analysis, calculated: C, 60.88; H, 3.73; N, 2.96, found: C, 61.01, H, 4.02; N, 2.85.

Example 6

The Preparation of Representative Osmium Phenanthroline Complexes

In this example, the synthesis of representative osmium phenanthroline complexes of the invention, [Os(II) (N—N)$_2$L—L]$^{2+}$2A$^-$, are described. A synthetic scheme for the preparation of representative osmium complexes having phenanthroline ligands is illustrated in FIG. 8. FIG. 8 includes a key identifying the compound numbers (i.e., 7-14), phenanthroline substituent (R), and bidentate ligand (L—L) by references number (i.e., 23-25).

The osmium complexes were prepared by reacting 1.00 g (2.08 mmol) K$_2$OsC16 with 2.05 equivalent of phenanthroline ligand (N—N) in 25 mL refluxing DMF for 3 hours under an inert atmosphere. The resulting solution was filtered, washed with DMF, cooled to 0° C., and then added dropwise to a water solution of sodium dithionite (2.00 g in 400 mL). The resulting purple precipitate of Os(N—N)$_2$Cl$_2$ was filtered and washed with deionized water. The Os(N—N)$_2$Cl$_2$ intermediate was reacted with 1.05 equivalent of bidentate ligand (L—L) in a refluxing mixture of 2,2'-ethoxyethoxyethanol and glycerol (75:25 by volume) for 2 hours under an inert atmosphere. The product complexes, Os(N—N)$_2$(L—L)$^{2+}$, 2A$^-$, were precipitated by dropwise addition of the intermediate solution to a water solution of the appropriate counter ion (e.g., tosylate, heptafluorobutyrate, and hexafluorophosphate).

The above procedure was used in the synthesis of the following osmium complexes.

Complex 7: [Osmium (II) (4,7-diphenyl-1,10-phenanthroline)$_2$ cis-1,2-bis(diphenylphosphino)ethylene]$^{2+}$ (triflate)$_2$. Yellow-orange product obtained in a yield of 92%. Mass spectrometry (m/2z): 626.2. Isotope pattern (m/2z): 623.7, 624.2, 624.7, 625.2, 625.7, 626.2, 626.7, 627.2, and 627.7, no fragmentation. Elemental analysis, calculated: C, 58.91%; H, 3.51%; N, 3.62%. Found C, 58.78; H, 3.52; N, 3.66.

Complex 8: [Osmium (II) (bathophenanthroline)$_2$ cis-1,2-vinylenebis(diphenylarsine)]$^{2+}$ (tosylate)$_2$. Red-orange product obtained in a yield of 90%. Mass spectrometry (m/2z): 670.1. Isotope pattern (m/2z): 667.6, 668.1, 668.6, 669.1, 669.6, 670.1, 670.6, 671.1, no fragmentation. Elemental analysis, calculated: C, 55.75%; H, 3.32%; N, 3.42%. Found C, 56.05; H, 3.34; N, 3.44.

Complex 9: [Osmium (II) (4,7-bis(p-methoxyphenyl)-1, 10-phenanthroline)$_2$ 1,2-bis(diphenylarseno)ethane]$^{2+}$ (tosylate)$_2$. Brick red product was obtained in a yield of 89%. Mass spectrometry m/2z=731.2. Isotope pattern: 728.7, 729.2, 729.7, 730.2, 730.7, 731.2, 731.7, 732.2, and 732.7. Fragment at m/2z-7.5 for loss of a methyl group. Elemental analysis, calculated: C, 61.26; H, 4.36; N, 3.11; found C, 61.36; H, 4.41; N, 3.05.

Complex 10: [Osmium (II) (4,7-bis(p-methoxyphenyl)-1, 10-phenanthroline)$_2$ cis-1,2-bis(diphenylphosphino)ethylene]$^{2+}$ (tosylate)$_2$. Yellow-orange product obtained in a yield of 95%. Mass Spectrometry m/2z=686.2. Isotope pattern: 683.7, 684.2, 684.7, 685.2, 685.7, 686.2, 686.2, 687.2, and 687.7. Fragment at m/2z-7.5 for the fragmentation of a methyl group. Elemental analysis, calculated: C, 64.47; H, 4.47; N, 3.27; found C, 64.57; H, 4.65; N, 3.25.

Complex 11: [Osmium (II) (4,7-bis(p-methoxyphenyl)-1, 10-phenanthroline)$_2$ cis-1,2-vinylenebis(diphenylarsine)]$^{2+}$ (tosylate 2. Red product was obtained in a 92% yield. Mass Spectrometry m/2z: 730.1. Isotope Pattern: 727.6, 728.1, 728.6, 729.1, 729.6, 730.1, 730.6, 731.1, and 731.6. Fragment appears at m/2z-7.5 for loss of a methyl group. Elemental analysis, calculated: C, 61.33; H, 4.25; N, 3.11; found: C, 61.64; H, 4.33; N, 3.12.

Complex 12: [Osmium (II) (4,7-bis(p-bromophenyl)-1,10-phenanthroline)$_2$ cis-1,2-vinylenebis(diphenylarsine)]$^{2+}$ (tosylate)$_2$. Dark red product was obtained in yield of 89%. Elemental analysis, calculated: C, 51.76; H, 3.31; N, 2.87, Found: C, 52.01; H, 3.38; N, 2.88. Mass spectrometry m/2z=827.9, isotope pattern 824.4, 824.9, 825.4, 825.9, 826.4, 826.9, 827.4, 827.9, 828.4, 828.9, 829.4, 829.9.

Complex 13: [Osmium (II) (4,7-bis(4'-phenoxybiphenyl-4-yl)-1,10-phenanthroline)$_2$ cis-12-vinylenebis(diphenylarsine)]$^{2+}$ (tosylate)$_2$. Red product was obtained in yield of 93%. Elemental analysis, calculated: C, 69.38; H, 4.28; N, 2.38; Found: C, 69.07; H, 4.36; N, 2.44. Mass Spectrometry m/2z=1006.1, isotope pattern 1004.2, 1004.7, 1005.2, 1005.7, 1006.2, 1006.7, 1007.2, 1007.7.

Complex 14: [Osmium (II) (4,7-bis(4-naphthalen-2-yl-phenyl)-1,10-phenanthroline)$_2$ cis-1,2-vinylenebis(diphenylarsine)]$^{2+}$ (tosylate)$_2$. Red product was obtained in yield of 88%. Elemental analysis, calculated: C, 70.25; H, 4.33; N, 2.56, Found: C, 70.56; H, 4.32; N, 2.48. Mass Spectrometry m/2z=922.7, isotope pattern 920.2, 920.7, 921.2, 921.7, 922.2, 922.7, 923.2, 923.7.

Example 7

Representative Osmium Phenanthroline Complexes

In this example, the optical properties of representative osmium phenanthroline complexes of the invention, [Os(II)(N—N)$^2$L—L]$^{2+}$ 2A$^-$, are described. The performance properties of LEDs including these osmium complexes is also described.

The four osmium complexes described in this example include two 4,7-disubstituted-1,10-phenanthroline ligands, a cis-1,2-bis(diphenylarsine)ethylene ligand, and two tosylate counter ions. The 4,7-substituents for each complex is the same (i.e., both 4 and 7-substituents are the same), but from complex to complex, the 4,7-substituents are different. The 4,7-substituents for the four complexes are (1) 4-(4'-trifluoromethyl biphenyl) or OsCF$_3$; (2) 1-dibenzothiophene or OsDBT; (3) 4-(4"-benzyloxytriphenyl) or OsTPE; and (4) 2-(7-ethoxynaphthalyl) or OsNPE. The structures of these substituents are shown below.

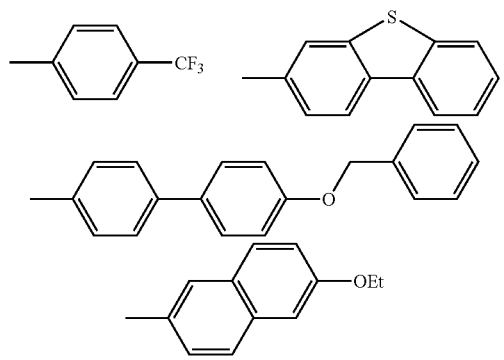

The absorbance and emission properties of these osmium complexes are summarized in Table 5 (absorption maxima for various ligand and charge transfer bands (nm); extinction coefficient ($\epsilon$); emission wavelength maxima (nm); luminescence lifetime ($\tau$, ns); and luminescence quantum yield ($\Phi$)).

TABLE 5

Optical Properties for Representative Osmium Complexes.

| Complex | LC (nm) ($\epsilon$) | $^1$MLCT (nm) | $^3$MLCT (nm) | Emission (nm) | $\tau$ (ns) | $\Phi$ |
|---|---|---|---|---|---|---|
| OsCF$_3$ | 305 (100,000) | 390 (39,000) | 500 (8,000) | 632 | 1300 | 0.43 |
| OsDBT | 286 (125,000) | 378 (43,000) | 500 (8,000) | 635 | 1200 | 0.37 |
| OsNPE | 285 (154,000) | 393 (78,000) | 500 (13,000) | 642 | 1200 | 0.42 |
| OsTPE | 277 (140,000) | 378 (63,000) | 500 (11,000) | 640 | 1650 | 0.40 |

The Os complexes demonstrate good phosphorescence quantum yields and short excited state lifetime, which are desirable properties for light-emitting diode applications. Double layer devices were fabricated using PVK/30% PBD and PF-OXD-TPA host materials. The $\pi$ system increases in the order of OsCF$_3$, OsDBT, OsTPE, OsNPE. In PVK this is the order in which brightness increases. However, efficiency remains largely unchanged with increasing $\pi$ system of the osmium complex. While the extended $\pi$ affects the strength of the charge transfer bands, the position of the bands is largely unchanged. The OsCF$_3$ MLCT is somewhat blue shifted from that of the other complexes. This may explain the small drop off in both brightness and efficiency for this complex. The primary overlap with PVK is with the spin forbidden charge transfer band. This is very little contribution from Förster energy transfer, and the primary source of emission is from trapping both holes and electrons on the osmium complex itself with little involvement from the host PVK material. As all the osmium complexes trap holes and electrons equally well, they all give similar efficiencies as expected.

LED devices were fabricated on ITO substrates that were cleaned and treated with O$_2$ plasma before use. A layer of about 40 nm thick hole-transport material (HTL), a tetraphenyldiamine containing perfluorocyclobutane polymer (BTPD-PFCB), was first fabricated by spin-coating the monomer from its 1,2-dichloroethane (DCE) solution and annealing at 225° C. under nitrogen atmosphere. Then a layer of 3.0 wt. % of Os complex doped blend of poly(N-vinylcarbazole) and 2-t-butylphenyl-5-biphenyl-1,3,4-oxadiazole (PVK:PBD, 70:30 by weight) or poly(fluorine) (PF) was spin coated from the corresponding DCE solution (about 12 mg/mL) at 2000 rpm. A layer of 30-nm-thick Ca was vacuum deposited at below $1\times10^{-6}$ torr through a mask in an argon protected evaporator, and another layer of 120-nm-thick Ag deposited as a protective layer. All testing was carried out in air at room temperature. Current-voltage characteristics were measured on a Hewlett Packard 4155B semiconductor parameter analyzer. EL spectra were measured with an Oriel InstaSpec IV CCD camera or a Photo Research PRR650 colorimeter. The EL emission power was measured using a Newport 2835-C multi-function optical meter in combination with a calibrated photodiode. Brightness was calculated from the emission power and EL spectra of the devices, assuming Lambertian distribution of the EL emission. Thickness of the films was measured on a Sloan Dektak 3030 profilometer.

The performance properties (voltage needed for 1 cd/m² brightness ($V_1$, V), maximum brightness ($B_{max}$, cd/m²), and maximum external quantum efficiency ($\eta_{max}$)) for two representative LEDs doped with the osmium complexes are summarized in Table 6: ITO//BTPD-PFCB//Os complex/PVK:PBD//Ca (Type I); and ITO//BTPD-PFCB//Os complex/PF-OXD-TPA//Ca (Type II).

TABLE 6

Performance Properties for LEDs Including Osmium Complexes.

| Os Complex | Device | $V_1$(V) | $B_{max}$(cd/m²) | $\eta_{max}$ |
|---|---|---|---|---|
| OsCF₃ | I | 7.5 | 1320 | .41 |
| OsDBT | I | 8.0 | 1580 | .47 |
| OsNPE | I | 8.0 | 1620 | .45 |
| OsTPE | I | 8.0 | 1610 | .47 |
| OsCF₃ | II | 8.0 | 2920 | 2.08 |
| OsNPE | II | 8.5 | 2400 | 2.32 |
| OsTPE | II | 6.5 | 1780 | 1.19 |

The PF-OXD-TPA host material offered a significantly blue shifted emission when compared to that of PVK:BPD, which created much better energy overlap between the host material and the charge transfer bands of the osmium complex dopant. The PF host material is a better conductor of both holes and electrons. The effect of these improvements is increased brightness and efficiency. While charge trapping at the osmium complex still takes place in the PF matrix, the increased overlap greatly increased the contribution from Forster energy transfer. What is observed as is the π system of the osmium complex is also a factor, which is unlike what is observed in the PVK:PBD host. The OsCF₃ has efficiency of 2.08% while the OsNPE has efficiency of 2.32%. This is due to the increased MLCT extinction coefficient of OsNPE (70,000 L·cm⁻¹·mol⁻¹) compared to that of OsCF₃ (30,000 L·cm⁻¹·mol⁻¹). Thus, there is larger overlap between OsNPE and PF increased efficiency is observed.

Example 8

Representative Osmium Bipyridine Complexes

In this example, the optical properties of representative osmium bipyridine complexes of the invention, [Os(II)(N—N)₂L—L]²⁺ 2A⁻, are described. The performance properties of LEDs including these osmium complexes is also described.

The four osmium complexes described in this example include two 4,4'-diphenyl-2,2'-bipyridine ligands. The complexes differ by their π-acid ligand and counter ions: (1) OsP includes a cis-1,2-bis(diphenylphosphine)ethylene ligand and two perfluorobutylate counter ions; (2) OsAs includes a 1,2-bis(diphenylarsine)ethane ligand and two perfluorobutylate counter ions; (3) OsPS includes a cis-1,2-bis(diphenylphosphine)ethylene ligand and two tosylate counter ions; and (4) OsAsD includes a cis-1,2-bis(diphenylphosphine)ethylene ligand and two perfluorobutylate counter ions.

LED devices were fabricated on ITO substrates that were cleaned and treated with O₂ plasma before use. For some LEDs, a layer of about 40 nm thick hole-transport material (HTL), a tetraphenyldiamine containing perfluorocyclobutane polymer (BTPD-PFCB), was first fabricated by spin-coating the monomer from its 1,2-dichloroethane (DCE) solution and annealing at 225° C. under nitrogen atmosphere. Then a layer of 3.0 wt. % of Os complex doped blend of poly(N-vinylcarbazole) and 2-t-butylphenyl-5-biphenyl-1,3,4-oxadiazole (PVK:PBD, 100:40 by weight) was spin coated from the corresponding DCE solution. Layers of Alq3 (optional) and Ca were vacuum deposited at below $1\times10^{-6}$ torr through a mask in an argon protected evaporator, and another layer of 120-nm-thick Ag deposited as a protective layer. All testing was carried out in air at room temperature. Current-voltage characteristics were measured on a Hewlett Packard 4155B semiconductor parameter analyzer. EL spectra were measured with an Oriel InstaSpec IV CCD camera or a Photo Research PRR650 colorimeter. The EL emission power was measured using a Newport 2835-C multi-function optical meter in combination with a calibrated photodiode. Brightness was calculated from the emission power and EL spectra of the devices, assuming Lambertian distribution of the EL emission. Thickness of the films was measured on a Sloan Dektak 3030 profilometer.

The performance properties (voltage needed for 1 cd/m² brightness ($V_1$, V), maximum brightness ($B_{max}$, cd/m²), maximum external quantum efficiency ($\eta_{max}$), and maximum photometric efficiency (P.E.$_{max}$, cd/A)) for representative LEDs doped with the osmium complexes are summarized in Table 7: ITO//BTPD-PFCB (0-40 nm)//Os complex (3 wt. %)/PVK:PBD (25-45 nm)//alq3 (0-25 nm)//Ca//Ag.

TABLE 7

Performance Properties for LEDs Including Osmium Complexes.

| $d_{HTL}$[a] (nm) | Os complex (thickness, nm) | $d_{Alq_3}$[b] (nm) | $V_1$[c] (V) | $B_{max}$[d] (cd/m²) | $\eta_{max}$[e] (%) | P.E.$_{max}$[f] (cd/A) |
|---|---|---|---|---|---|---|
| 0 | OsAs (45) | 0 | 9.0 | 140 | 0.23 | 0.11 |
| 40 | OsAs (45) | 0 | 9.3 | 310 | 0.64 | 0.31 |
| 40 | OsAs (25) | 25 | 7.0 | 590 | 0.82 | 0.40 |
| 0 | OsP (45) | 0 | 7.5 | 260 | 0.27 | 0.23 |
| 40 | OsP (45) | 0 | 8.6 | 490 | 0.73 | 0.69 |
| 40 | OsP (25) | 25 | 6.5 | 730 | 0.63 | 0.65 |
| 40 | OsPS (45) | 0 | 8.7 | 970 | 0.27 | 0.27 |
| 40 | OsAsD (45) | 0 | 7.6 | 410 | 0.60 | 0.35 |

[a]Thickness of BTPD-PFCB layer.
[b]Thickness of Alq₃ layer.
[c]Voltage needed for brightness of 1 cd/m².
[d]Maximum brightness.
[e]Maximum external quantum efficiency.
[f]Maximum photometric efficiency.

The EL emission of OsAs peaks at 650 nm. Compared with OsAs, the double-bonding linkage between the two AS atoms in OsAsD enhances the photoluminescence emission and blueshifts the emission peak by about 10 to 640 nm. The emission of OsP and OsPS is identical and peaks at about 620 nm, because the two complexes only differ in counter ions. Even with a single-layer structure ITO//PVK:PBD:OsAs// Ca, an external quantum efficiency of 0.23% and brightness of 140 cd/m² were achieved. When a hole-transporting layer (HTL) of BTPD-PFCB was introduced, the efficiency and brightness of the LED device were more than doubled. With a three-layer ITO//HTL//PVK:PBD:OsAs//Alq$_3$//Ca configuration high efficiency (0.82%) and brightness (590 cd/m²) were obtained, clearly demonstrating that OsAs useful in red emitting LED applications. The quality of emission spectra with regard to color and saturation are typically defined by their Commission Internationale de l'Eclairage (CIE) chromaticity coordinates x y. The CIE coordinates (x,y) for OsP, OsPS, OsAs, and OsAsD are (0.60, 0.39), (0.61, 0.39), (0.65, 0.33), and (0.65, 0.34), respectively. The coordinates change slightly with the voltage because the emission wavelength of the devices shifts towards red as the applied voltage increases. It should be noted that changing the counter ion from heptafluorobutyrate in OsP to tosylate in OsPs increases the brightness of the device while it decreases the efficiency. This indicates that the role of counter ions is also important for optimizing the device performance.

The osmium complex doped devices also showed much smaller current than the undoped PVK:PBD devices. To study the carrier trapping property of the complexes, hole-only devices were fabricated using ITO as anode and Au as cathode, and electron-only devices fabricated using Al as anode and Ca as cathode. After the doping of OsP, both the hole and electron currents drop compared with the undoped PVK:PBD devices. Therefore, the osmium complexes act as traps for both the holes and electrons. The π orbital of the bipyridine ligands in the complexes is the lowest-energy unoccupied state and should be easily reduced, making it the likely trap site for electrons. On the other hand, the d orbital of the Os(II) ion in the complexes is the highest occupied state, making it the likely site for oxidation and, thus, trap site of holes. The trapping of holes and electrons on the osmium complex can facilitate the direct recombination of the holes and electrons on it, which eliminates the process of energy transfer from the host to the osmium complexes and can potentially enhance the device efficiency.

Example 9

The Preparation of Representative Green-Emitting Osmium Complexes

In this example, the synthesis of a representative green-emitting osmium complex of the invention is described: [osmium (II) (1,10-phenanthroline) bis(cis-1,2-vinylenebis(diphenylarsine))]²⁺ (hexafluorophosphate)$_2$ and [osmium (II) (1,10-phenanthroline) bis(cis-1,2-vinylenebis(diphenylphosphine))]²⁺ (hexafluorophosphate)$_2$ To a solution of (NH$_4$)$_2$OsCl$_6$ (1 g) in 50 mL 3N aqueous hydrochloric acid was added a solution of phenanthroline dissolved in a minimal amount of 3N aqueous hydrochloric acid. A precipitate was formed and the solution was cooled on an ice bath. The precipitate was filtered and washed with large amount of cold water and dried under vacuum. The precipitate was pyrolyzed in the solid state at 290° C. under argon. The brown-yellow product, OsCl$_4$(1,10-phenanthroline), was used in further reactions without further purification. The resulting brown product was reacted with 2 equivalents of either cis-1,2-vinylenebis(diphenylarsine) or cis-1,2-vinylenebis(diphenylphosphine) in glycerol/ethoxyethoxyethanol mixture as described for the other complexes. The resulting solution was precipitated in water with potassium hexafluorophosphate. The precipitate was filtered, dried, and then column chromatography was performed (dichloromethane, basic alumina) eluting a yellow band.

The optical properties of these complexes are described in Table 3 above. The performance of these compounds in a LED is described in Table 4 above.

Example 10

Representative Device Fabrication

Representative light-emitting devices of the invention were fabricated on ITO substrates that were cleaned and treated with O$_2$ plasma before use. A layer of about 40 nm thick hole-transport material (HTL), a tetraphenyldiamine containing perfluorocyclobutane polymer (BTPD-PFCB), was first fabricated by spin-coating the monomer from its 1,2-dichloroethane (DCE) solution and annealing at 225° C. under nitrogen atmosphere. Following spin-coating of the HTL material, a layer of 3.0 weight percent representative osmium complex in a doped blend of poly(N-vinylcarbazole) and 2-t-butylphenyl-5-biphenyl-1,3,4-oxadiazole (PVK:PBD, 70:30 by weight) was spin coated from the corresponding DCE solution (about 12 mg/mL) at 2000 rpm. A layer of 30-nm-thick calcium (Ca) was vacuum deposited at less than 1×10⁻⁶ torr through a mask in an argon protected evaporator, and another layer of 120-nm-thick Ag deposited as a protective layer.

All testing was carried out in air at room temperature. Current-voltage characteristics were measured on a Hewlett Packard 4155B semiconductor parameter analyzer. Electroluminescent spectra were measured with an Oriel InstaSpec IV CCD camera or a Photo Research PR650 calorimeter. The electroluminescent emission power was measured using a Newport 2835-C multi-function optical meter in combination with a calibrated photodiode. Brightness was calculated from the emission power and EL spectra of the devices, assuming Lambertian distribution of the EL emission, and confirmed with the PR650 colorimeter. Thickness of the films was measured on a Sloan Dektak 3030 profilometer. Performance of representative devices is summarized in Table 2, FIG. 12.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A composition, comprising an osmium complex having the formula:

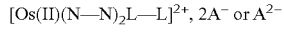

wherein Os(II) comprises divalent osmium;

N—N comprises a 2,2'-bipyridine ligand substituted with aryl, arylalkyl, alkenyl, alkoxy, amino, alkylamino, dialkylamino, or halogen, or a substituted or unsubstituted 1,10-phenanthroline ligand;

L—L comprises a π-acid bidentate ligand; and

A comprises a counter ion;

and a host material, the host material having an emission spectrum and the osmium complex having an absorbance spectrum, wherein the host material emission spectrum and the osmium complex absorbance spectrum have a spectral overlap sufficient to effect energy transfer from the host material to the osmium complex.

2. The composition of claim 1, wherein the host material is at least one of an organic compound, an organometallic compound, or a polymer.

3. The composition of claim 1, wherein the host material is at least one of 2,9-dimethyl-4,7-diphenyl-1,10-phenanthroline, 4,4'-N,N'-dicarbazole biphenyl, 1,3-bis(N,N-t-butylphenyl)-1,3,4-oxadiazole), 3-phenyl-4-(1'-naphtlhyl)-5-phenyl-1,2,4-triazole), or (4,4'-bis[N-(1-naphthyl)-N-phenyl-amino]biphenyl).

4. The composition of claim 1, wherein the host material is at least one of copper phthalocyanine, aluminum tris(8-hydroxyquinolate), or (1,1'-biphenyl)-4-olato)bis(2-methyl-8-quinolinolato N1,O8)aluminum.

5. The composition of claim 1, wherein the host material is at least one of poly(N-vinylcarbazole), 2-t-butylphenyl-5-biphenyl-1,3,4-oxadiazole, poly(2-vinylnaphthalene), poly(fluorene), a poly(fluorene) derivative, or a blue-emitting conjugated polymer.

6. The composition of claim 1, wherein the host material comprises (poly[(9,9-bis(4-di(4-n-butylphenyl)aminophenyl))]-stat(9,9-bis(4-(5-(4-tert-butylphenyl)-2-oxadiazolyl)-phenyl))-stat-(9,9-di-n-octyl)fluorene).

7. The composition of claim 1, wherein the host material comprises a blend of poly(N-vinylcarbazole) and 2-t-butylphenyl-5-biphenyl-1,3,4-oxadiazole.

8. The composition of claim 1, wherein the host material comprises a blend of poly(2-vinylnaphthalene) and 2-t-butylphenyl-5-biphenyl-1,3,4-oxadiazole.

9. The composition of claim 1, wherein the osmium complex is present in an amount from about 1 to about 15 percent by weight of the host material.

10. An emissive layer for a light-emitting device, comprising an osmium complex having a formula:

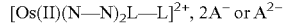

wherein Os(II) comprises divalent osmium;
N—N comprises a 2,2'-bipyridine ligand substituted with aryl, arylalkyl, alkenyl, alkoxy, amino, alkylamino, dialkylamino, or halogen, or a substituted or unsubstituted 1,10-phenanthroline ligand;
L—L comprises a π-acid bidentate ligand; and
A comprises a counter ion; and
a host material, the host material having an emission spectrum and the osmium complex having an absorbance spectrum, wherein the host material emission spectrum and the osmium complex absorbance spectrum have a spectral overlap sufficient to effect energy transfer from the host material to the osmium complex.

11. An organic light-emitting device comprising:
a hole injecting anode layer;
an electron injecting cathode layer; and
at least one emissive layer comprising an osmium complex having a formula:

wherein Os(II) comprises divalent osmium;
N—N comprises a 2,2'-bipyridine ligand substituted with aryl, arylalkyl, alkenyl, alkoxy, amino, alkylamino, dialkylamino, or halogen, or a substituted or unsubstituted 1,10-phenanthroline ligand;
L—L comprises a α-acid bidentate ligand; and
A comprises a counter ion; and
a host material, the host material having an emission spectrum and the osmium complex having an absorbance spectrum, wherein the host material emission spectrum and the osmium complex absorbance spectrum have a spectral overlap sufficient to effect energy transfer from the host material to the osmium complex;
wherein the emissive layer is intermediate the hole injecting anode layer and the electron injecting cathode layer.

12. A method for making a light-emitting device, comprising:
(a) applying an osmium complex and a host material to a substrate to provide an emissive layer, wherein the osmium complex has the formula:

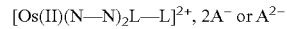

wherein Os(II) comprises divalent osmium;
N—N comprises a 2,2'-bipyridine ligand substituted with aryl, arylalkyl, alkenyl, alkoxy, amino, alkylamino, dialkylamino, or halogen, or a substituted or unsubstituted 1,10-phenanthroline ligand;
L—L comprises a π-acid bidentate ligand; and
A comprises a counter ion;
wherein the host material has an emission spectrum and the osmium complex has an absorbance spectrum, wherein the host material emission spectrum and the osmium complex absorbance spectrum have a spectral overlap sufficient to effect energy transfer from the host material to the osmium complex; and
(b) depositing an electron injection material onto the emissive layer to provide an electron injection cathode layer.

13. The composition of claim 1, wherein the aryl group is selected from the group consisting of phenyl, biphenyl, 4-phenoxybiphenyl, and triphenyl.

14. The composition of claim 1, wherein the substituted-1,10-phenanthroline is selected from the group consisting of 4,7-diphenyl-1,10-phenanthroline, 4,7-bis-(4-methoxyphenyl)-[1,10]phenanthroline, 4,7-bis-(4-bromophenyl)-[1,10]phenanthroline, 4,7-bis-(4'-phenoxybiphenyl-4-yl)-[1,10]phenanthroline, 4,7-bis-(4-naphthalen-2-yl-phenyl)-[1,10]phenanthroline, 4,7-bis-(4'-trifluoromethylbiphenyl-4-yl)-[1,10]phenanthroline, 4,7-bis-(4-dibenzothiophen-4-yl-phenyl)-[1,10]phenanthroline, 4,7-bis-(4"-benzyloxy-[1,1'; 4',1"]terphenyl-4-yl)-[1,10]phenanthroline, and 4,7-bis-[4-(6-ethoxynaphthalen-2-yl)-phenyl]-[1,10]phenanthroline.

15. The emissive layer of claim 10, wherein the aryl group is selected from the group consisting of phenyl, biphenyl, 4-phenoxybiphenyl, and triphenyl.

16. The emissive layer of claim 10, wherein the substituted-1,10-phenanthroline is selected from the group consisting of 4,7-diphenyl-1,10-phenanthroline, 4,7-bis-(4-methoxyphenyl)-[1,10]phenanthroline, 4,7-bis-(4-bromophenyl)-[1,10]phenanthroline, 4,7-bis-(4'-phenoxybiphenyl-4-yl)-[1,10]phenanthroline, 4,7-bis-(4-naphthalen-2-ylphenyl)-[1,10]phenanthroline, 4,7-bis-(4'-trifluoromethylbiphenyl-4-yl)-[1,10]phenanthroline, 4,7-bis-(4-dibenzothiophen-4-yl-phenyl)-[1,10]phenanthroline, 4,7-bis-(4"-benzyloxy-[1,1'; 4",1"]terphenyl-4-yl)-[1,10]phenanthroline, and 4,7-bis-[4-(6-ethoxynaphthalen-2-yl)-phenyl]-[1,10]phenanthroline.

17. The device of claim 11, wherein the aryl group is selected from the group consisting of phenyl, biphenyl, 4-phenoxybiphenyl, and triphenyl.

18. The device of claim 11, wherein the substituted-1,10-phenanthroline is selected from the group consisting of 4,7-diphenyl-1,10-phenanthroline, 4,7-bis-(4-methoxyphenyl)-[1,10]phenanthroline, 4,7-bis-(4-bromophenyl)-[1,10]phenanthroline, 4,7-bis-(4'-phenoxybiphenyl-4-yl)-[1,10]phenanthroline, 4,7-bis-(4-naphthalen-2-ylphenyl)-[1,10]phenanthroline, 4,7-bis-(4'-trifluoromethylbiphenyl-4-yl)-[1,10]phenanthroline, 4,7-bis-(4-dibenzothiophen-4-yl-phenyl)-[1,10]phenanthroline, 4,7-bis-(4"-benzyloxy-[1,1', 4',1"]terphenyl-4-yl)-[1,10]phenanthroline, and 4,7-bis-[4-(6-ethoxynaphthalen-2-yl)-phenyl]-[1,10]phenanthroline.

19. The method of claim 12, wherein the aryl group is selected from the group consisting of phenyl, biphenyl, 4-phenoxybiphenyl, and triphenyl.

20. The method of claim 12, wherein the substituted-1,10-phenanthroline is selected from the group consisting of 4,7-diphenyl-1,10-phenanthroline, 4,7 bis-(4-methoxyphenyl)-[1,10]phenanthroline, 4,7-bis-(4-bromophenyl)-[1,10]phenanthroline, 4,7-bis-(4'-phenoxybiphenyl-4-yl)-[1,10]phenanthroline, 4,7-bis-(4-naphthalen-2-yl-phenyl)-[1,10]phenanthroline, 4,7-bis-(4'-trifluoromethylbiphenyl-4-yl)-[1,10]phenanthroline, 4,7-bis-(4-dibenzothiophen-4-yl-phenyl)-[1,10]phenanthroline, 4,7-bis-(4"-benzyloxy-[1,1'; 4',1"]terphenyl-4-yl)-[1,10]phenanthroline, and 4,7-bis-[4-(6-ethoxynaphthalen-2-yl)-phenyl]-[1,10]phenanthroline.

21. The composition of claim 1, wherein halogen is bromide.

22. The emissive layer of claim 10, wherein halogen is bromide.

23. The device of claim 11, wherein halogen is bromide.

24. The method of claim 12, wherein halogen is bromide.

* * * * *

UNITED STATES PATENT AND TRADEMARK OFFICE
CERTIFICATE OF CORRECTION

PATENT NO. : 7,416,791 B1
APPLICATION NO. : 10/460054
DATED : August 26, 2008
INVENTOR(S) : W. B. Carlson et al.

Page 1 of 1

It is certified that error appears in the above-identified patent and that said Letters Patent is hereby corrected as shown below:

| COLUMN | LINE | ERROR |
|---|---|---|
| 27 | 63 | "a α-acid" should read --a π-acid-- |

Signed and Sealed this

Eighth Day of September, 2009

David J. Kappos
*Director of the United States Patent and Trademark Office*